United States Patent
Chang et al.

(10) Patent No.: US 6,653,465 B2
(45) Date of Patent: Nov. 25, 2003

(54) SPLICED GENE OF KSHV / HHV8, ITS PROMOTER AND MONOCLONAL ANTIBODIES SPECIFIC FOR LANA2

(75) Inventors: Yuan Chang, Irvington, NY (US); Patrick S. Moore, Irvington, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/733,728

(22) Filed: Dec. 8, 2000

(65) Prior Publication Data

US 2002/0137020 A1 Sep. 26, 2002

(51) Int. Cl.$^7$ ...................... C07H 21/04; A61K 39/245; A61K 39/12
(52) U.S. Cl. ................. 536/24.1; 424/229.1; 424/199.1; 435/91.1; 435/325
(58) Field of Search ........................... 424/199.1, 229.1; 435/91.1, 325, 235.1, 239; 514/44; 536/24.1

(56) References Cited

U.S. PATENT DOCUMENTS

| | | | |
|---|---|---|---|
| 5,801,042 A | 9/1998 | Chang et al. |
| 5,830,759 A | 11/1998 | Chang et al. |
| 6,150,093 A | 11/2000 | Chang et al. |

FOREIGN PATENT DOCUMENTS

| | | |
|---|---|---|
| WO | WO9606159 | 2/1996 |
| WO | WO9727208 | 7/1997 |
| WO | WO9804576 | 2/1998 |

OTHER PUBLICATIONS

Ballestas, Mary E., et al. (1999) "Efficient Persistence of Extrachromosomal KSHV DNA Mediated by Latency–Associated Nuclear Antigen" *Science*, 284:641–644 (Exhibit 1).
Dittmer, Dirk, et al. (1998), "A Cluster of Latently Expressed Genes in Kaposi's Sarcoma–Associated Herpesvirus" *Journal of Virology*, 72:8309–8315, (Exhibit 2).
Dupin, Nicolas, et al. (1999) "Distribution of Human Herpesivirus–8 Latently Infected Cells in Kaposi's Sarcoma, Multicentric Castleman's Disease, and Primary Effusion Lymphoma", *PNAS* 96:4546–4551, (Exhibit 3).
Friborg, Jacques Jr., et al. (1999) "p53 Inhibition by the LANA Protein of KSHV Protects Against Cell Death", *Nature* 402:889–894, (Exhibit 4).
Katano, Harutaka, et al. (2000) "Expression and Localization of Human Herpesvirus 8–Encoded Proteins in Primary Effusion Lymphoma, Kaposi's Sarcoma, and Multicentric Castleman's Disease", *Virology* 269:335–344, (Exhibit 5).
Neipel, Frank, et al. (1997) "Cell–Homologous Genes in the Kaposi's Sarcoma–Associated Rhadinovirus Human Herpesvirus 8: Determinants of Its Pathogenicity?", *Journal of Virology* 71:4187–4192, (Exhibit 6); and.

Russo, James J., et al. (1996) "Nucleotide Sequence of Kaposi Sarcoma–Associated Herpesvirus (HHV8)", *PNAS* 93: 14862–14867 (Exhibit 7).
Alexander, L: et al., (2000) "The Primary Sequence of Rhesus Monkey Rhadinovirus Isolate 26–95: Sequence Similarities To Kaposi's Sarcoma–Associated Herpesvirus And Rhesus Monkey Rhadinovirus Isolate 17577" *J. Virol.* 74:3388–98 (Exhibit 1).
Bais, C. et al., (1998) "G–Protein–Coupled Receptor Of Kaposi's Sarcoma–Associated Herpesvirus Is A Viral Oncogene And Angiogenesis Activator" *Nature* 391:86–9 (Exhibit 2).
Ballestas, M. E. et al., (1999) "Efficient Persistence Of Extrachromosomal KSHV DNA Mediated By Latency–Associated Nuclear Antigen" *Science* 284:641–4 (Exhibit 3).
Burysek, L. et al., (1999) "Functional Analysis Of Human Herpesvirus 8–Encoded Viral Interferon Regulatory Factor 1 And Its Association with Cellular Interferon Regulatory Factors And p300" *J. Virol.* 73:7334–42 (Exhibit 4).
Burysek, L. et al., (1999) "Unique Properties Of A Second Human Herpesvirus 8–Encoded Interferon Regulatory Factor (vIRF–2)" *J. Hum. Virol.* 2:19–32 (Exhibit 5).
Cesarman, E. et al., (1995) "Kaposi's Sarcoma–Associated Herpesvirus–Like DNA Sequences In AIDS–Related–Body––Cavity–Based Lymphomas" *New Eng. J. Med.* 332:1186–1191 (Exhibit 6).
Chang, Y. et al., (1996) "Cyclin Encoded By KS Herpesvirus" *Nature* 382:410 (Exhibit 7).
Chang, Y., et al., (1994) "Identification Of Herpes–Like DNA Sequences In AIDS–Associated Kaposi's Sarcoma", *Science* 265:1865–1869 (Exhibit 44).
Davis, M. A., et al., (1997) "Expression Of Human Herpesvirus 8–Encoded Cyclin D In Kaposi's Sarcoma Spindle Cells" *J. Natl. Cancer Inst.* 89:1868–74 (Exhibit 8).
Dittmer, D., et al., (1998) "A Cluster Of Latently Expressed Genes In Kaposi's Sarcoma–Associated Herpesvirus" *J. Virol.* 72:8309–15 (Exhibit 9).
Dupin, N., et al., (1999) "Distribution Of Human Herpesvirus–8 Latently Infected Cells In Kaposi's Sarcoma, Multicentric Castleman's Disease, And Primary Effusion Lymphoma" *Proc. Natl. Acad Sci. U.S.A.* 96:4546–51 (Exhibit 10).

(List continued on next page.)

Primary Examiner—Ali R. Salimi
(74) Attorney, Agent, or Firm—John P. White; Cooper & Dunham LLP

(57) ABSTRACT

This invention provides an isolated nucleic acid which encodes a Kaposi's sarcoma-associated herpesvirus latency-associated nuclear antigen 2 polypeptide (LANA2) or a fragment thereof and also provides the LANA2 polypeptide. This invention provides an isolated nucleic acid comprising consecutive nucleotides having the sequence of a promoter of Kaposi's sarcoma-associated herpesvirus latency-associated nuclear antigen 2 transcription. This invention also provides a method of inhibiting p53 mediated apoptosis of a cell and a method of producing an antibody which comprises introducing into a cell a replicable vector of the subject invention.

3 Claims, 14 Drawing Sheets

OTHER PUBLICATIONS

Flowers, C., et al., (1998) "Kaposi's Sarcoma–Associated Herpesvirus Viral Interferon Regulatory Factor Confers Resistance To The Antiproliferative Effect Of Interferon–Alpha" *Mol. Med.* 4:402–12 (Exhibit 11).

Friborg, J., et al., (1999) "p53 Inhibition By The LANA Protein Of KSHV Protects Against Cell Death" *Nature* 402:889–94 (Exhibit 12).

Gao, S.–J., et al., (1997) "KSHV ORF K9 (vIRF) Is An Oncogene Which Inhibits The Interferon Signaling Pathway" *Oncogene* 15:1979–85 (Exhibit 13).

Gao, S. J., et al., (1996) "KSHV antibodies among Americans, Italians And Ugandans With And Without Kaposi's Sarcoma" *Nature Medicine* 2:925–8 (Exhibit 14).

Godden–Kent, D., et al., (1997) "The cyclin encoded by Kaposi's Sarcoma–Associated Herpesvirus Stimulates cdk6 To Phosphorylate The Tetinoblastoma Protein And Histone H1" *Journal of Virology* 71:4193–8 (Exhibit 15).

Gu, W., et al., (1997) "Activation Of p53 Sequence–Specific DNA Binding By Acetylation Of The p53 C–Terminal Domain" *Cell* 90:595–606 (Exhibit 16).

Jayachandra, S., et al., (1999) "Three Unrelated Viral Transforming Proteins (vIRF, EBNA2, and E1A) Induce The MYC Oncogene Through The Interferon–Responsive PRF Element By Using Different Transcription Coadaptors" *Proc. Natl. Acad. Sci. U.S.A.* 96:11566–11571 (Exhibit 17).

Judde, J. G., et al., (2000) "Monoclonality or Oligoclonality of Human Herpesvirus 8 Terminal Repeat Sequences in Kaposi's Sarcoma And Other Diseases" *J. Natl. Cancer Inst.* 92:729–736B (Exhibit 18).

Katano, H., et al., (2000) "Expression And Localization Of Human Herpesvirus 8–Encoded Proteins In Primary Effusion Lymphoma, Kaposi's Sarcoma, And Multicentric Castleman's Disease" *Virology* 269:335–44 (Exhibit 19).

Katano, H., et al., (1999) "High Expression Of HHV–8–Encoded ORF73 Protein In Spindle–Shaped Cells Of Kaposi's Sarcoma" *Am. J. Pathol.* 155:47–52 (Exhibit 20).

Kirshner, J. R., et al., (1999) "Expression Of The Open Reading Frame 74 (G–Protein–Coupled Receptor) Gene Of Kaposi's Sarcoma (KS)–Associated Herpesvirus: Implications For KS Pathogenesis" *J. Virol.* 73:6006–14 (Exhibit 21).

Lee, H., et al., (1998) "Deregulation Of Cell Growth By The K1 Gene Of Kaposi's Sarcoma–Associated Herpesvirus" *Nat. Med.* 4:435–40 (Exhibit 22).

Li, M., et al., (1998) "Kaposi's Sarcoma–Associated Viral Interferon Regulatory Factor" *J. Virol.* 72:5433–40 (Exhibit 23).

Li, M., et al., (1997) "Kaposi's Sarcoma–Associated Herpesvirus Encodes A Functional Cyclin" *Journal of Virology* 71:1984–91 (Edhibit 24).

Moore, P. S., et al., (1996) "Molecular Mimicry Of Human Cytokine And Cytokine Response Pathway Genes By KSHV" *Science* 274:1739–1744 (Exhibit 25).

Moore and Chang (1995) "Detection Of Herpesvirus–like DNA Sequences In Kaposi's Sarcoma In Patients With And Those Without HIV infection" *New Eng. J. Med.* 332:1181–1185 (Exhibit 45).

Moore, et al., (1996) "Primary Characterization Of A Herpesvirus Agent Associated With Kaposi's Sarcoma" *J. Virol.* 70(1):549–558 (Exhibit 46).

Neipel, F., et al., (1997) "Cell–Homologous Genes In The Kaposi's Sarcoma–Associated Rhadinovirus Human Herpesvirus 8: Determinants Of Its Pathogenicity?" *Journal of Virology* 71:4187–92 (Exhibit 26).

Ojala, P. M., et al., (1999) "Kaposi's Sarcoma–Associated Herpesvirus–Encoded v–Cyclin Triggers Apoptosis In Cells With High Levels Of Cyclin–Dependent Kinase 6" *Cancer Res.* 59:4984–9 (Exhibit 27).

Parravicini, C., et al., (2000) "Differential Viral Protein Expression In Kaposi's Sarcoma–Associated Herpesvirus––Infected Diseases: Kaposi's Sarcoma, Primary Effusion Lymphoma, And Multicentric Castleman's Disease" *Am. J. Pathol.* 156:743–9 (Exhibit 28).

Reed, J. A., et al., (1998) "Demonstration Of Kaposi's Sarcoma–Associated Herpes Virus Cyclin D Homolog In Cutaneous Kaposi's Sarcoma By Colorimetric In Situ Hybridization Using A Catalyed Signal Amplification System" *Blood* 91:3825–32 (Exhibit 29).

Russo, J. J., et al., (1996) "Nucleotide Sequence Of The Kaposi Sarcoma–Associated Herpesvirus (HHV8)" *Proc. Natl. Acad. Sci. U.S.A.* 93:14862–7 (Exhibit 30).

Sarid, R., et al., (1998) "Transcription Mapping Of The Kaposi's Sarcoma–Associated Herpesvirus (human herpesvirus 8) Genome In A Body Cavity–Based Lymphoma Cell Line (BC–1)" *J. Virol.* 72:1005–12 (Exhibit 31).

Sarid, R., et al., (1997) "Kaposi's Sarcoma–Associated Herpesvirus Encodes A Functional bcl–2 Homologue" *Nature Medicine* 3:293–8 (Exhibit 32).

Sarid, R., et al., (1999) "Characterization And Cell Cycle Regulation Of The Major Kaposi's Sarcoma–Associated Herpesvirus (Human Herpesvirus 8) Latent Genes And Their Promoter" *J. Virol.* 73:1438–46 (Exhibit 33).

Sun, R., et al., (1999) "Kinetics Of Kaposi's Sarcoma–Associated Herpesvirus Gene Expression" *J. Virol.* 73:2232–42 (Exhibit 34).

Takebe, Y., et al., (1988) "SRα promoter: An Efficient And Versatile Mammalian cDNA Expression System Composed Of The Simian Virus 40 Early Promoter And The R–U5 Segment Of The Human T–Cell Leukemia Virus Type 1 Long Terminal Repeat" *Mol. Cell Biol.* 8:466–72 (Exhibit 35).

Talbot, S. J., et al., (1999) "Transcriptional Analysis Of Human Herpesvirus–8 Open Reading Frames 71, 72, 73, K14, and 74 In A Primary Effusion Lymphoma Cell Line" *Virology* 257:84–94 (Exhibit 36); and.

Zimring, J. C., et al., (1998) "Human Herpesvirus 8 Encodes An Interferon Regulatory Factor (IRF) Homolog That Represses IRF–1–Mediated Transcription" *J. Virol.* 72:701–7 (Exhibit 37).

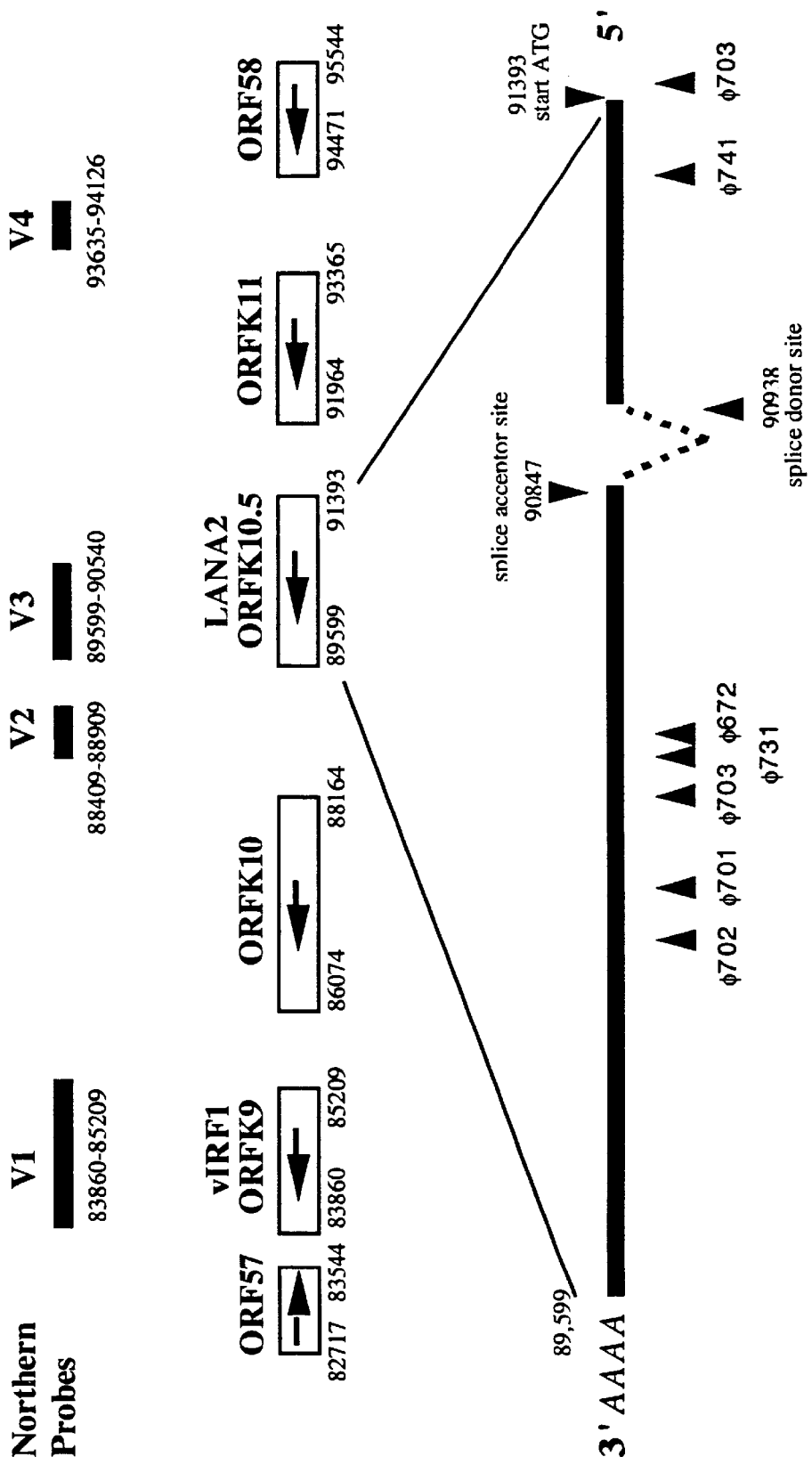

Figure 7
Panel A
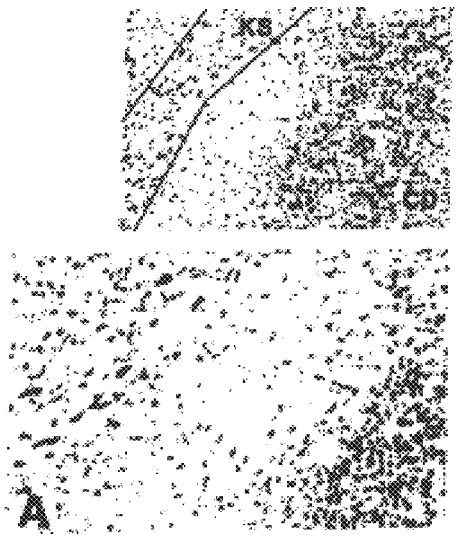
Panel B
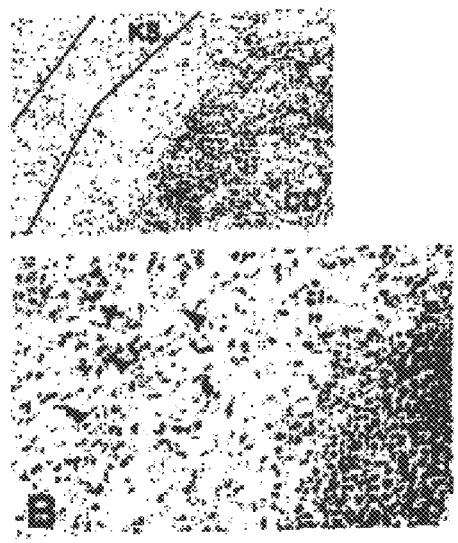

FIGURE 11

|  | Number | Western blot ORF65 | Western blot LANA1 | IFA LANA1 | Western blot LANA2 |
|---|---|---|---|---|---|
| AIDS-KS | 4 | 4/4 |  | 4/4 | 0/4 |
| Classical KS | 4 | 4/4 |  | 4/4 | 0/4 |
| Multicentric Castleman's | 4 | 4/4 |  | 4/4 | 0/4 |
| PEL | 2 | 2/2 |  | 2/2 | 0/2 |
| Blood donors | 4 | 0/4 |  | 0/4 | 0/4 |
| LANA2 hybridoma Clones * | 2 | ND |  | ND | 2/2 |

Figure 12

```
ATGGCGGGACGCAGGCTTACCTGGATTTCTGAGTTTATTGTAGGTGCTTTGG
ACTCTGATAAATATCCTTTGGTCAAGTGGCTAGATAGATCTACTGGAACATT
TCTTGCTCCGGCTGCCCGTAATGACGTAATTCCTCTGGATAGCCTACAGTTTT
TCATTGATTTTAAGAGGGAATGCCTATCGAAGGGCCTGCATCCCAGAGATTT
ACTGGGCTCGCCGATTACGGCTTTTGGGAAAATATGTACCACGTCGCGGCGC
CTTAGACGCTTGCCAGGTGAAGAGTACGAGGTCGTACAGGGAATTAATTGTA
GAAGGTGGCGCCTCCTGTGTGCCGAGGTAAAGGAATGCTGGTGGTGCGTTCA
TGCCAGGACTCACCTACACAGTGGGTCATCACTATGGGAAATTTTGTATCAA
CACAGTGTACGGCTCGAGAAGCATCGGAGAAGACCAAGGAGGCCATTTGTG
GGTGAAAACTCGGATTCCAGTGAGGAGGATCACCCAGCCTTTTGCGATGTGC
CGGTCACGCAGACGGGCGCGGAATCTGAGGACTCTGGAGACGAGGGACCAT
CGACGCGCCATAGTGCGTCTGGGGTTCAGCCAGTTGATGATGCCAATGCCGA
CTCTCCTGGCTCTGGAGACGAAGGACCCTCGACGCGTCATAGCGACTCGCAG
CCCCCCCCGGCCGATGAAACAACGGTGCACACAGACAACGTTGAAGATGAC
CTCACACTGCTTGATAAAGAATCTGCATGTGCATTGATGTACCACGTGGGAC
AGGAGATGGACATGCTAATGAGGGCGATGTGCGATGAAGACCTCTTTGATCT
GCTTGGCATCCCAGAGGATGTTATCGCAACATCACAGCCCGGAGGCGACAC
GGATGCAAGCGGCGTGGTAACAGAGGGCTCAATCGCCGCCTCGGCTGTCGG
GGCGGGTGTAGAGGATGTGTACTTAGCTGGGGCACTCGAGGCCCAGAATGT
AGCAGGGGAATATGTGTTGGAGATAAGTGACGAAGAAGTCGATGATGGTGC
TGGACTGCCGCCGGCGTCCAGACGCCGGCCAGTTGTTGGCGAATTTTTATGG
GATGATGGGCCACGGAGACACGAGAGGCCTACCACGAGGCGCATTCGCCAC
AGGAAGCTTAGATCCGCATATTATAGAGTGGCACGGCCGCCAGTAATGATA
ACCGATAGGCTTGGTGTGGAAGTGTTTTATTTTGGCCGCCCTGCAATGTCTTT
GGAAGTGGAACGAAAGGTGTTTATTCTATGTTCCCAGAACCCACTGGCAGAC
ATTAGCCACTCTTGCTTGCATTCGCGCAAAGGGTTAAGAGTTTTGTTGCCCA
AACCTGACGACAATAACACAGGGCCAGGAGACGTTAACCTGCTGGCGGCCG
TGCTGCGCTCGTTTGCTTCGGGTCTTGTGATAGTTTCTCTCCGATCTGGCATT
TATGTTAAGAATTTGTGCAAGTCTACCGTATTATATCATGGAAATAATCCTC
CAAAGAAGTTTGGTGTGATCTGCGGACTGTCATCTAGGGCTGTTCTGGATGT
TTTTAATGTGGCACAATATCGCATACAGGGACATGAGCACATTAAAAAAACA
ACTGTGTTCATCGGAGGTGACCCAACGTCGGCAGAACAGTTCGATATGGTCC
CCCTCGTCATCAAGCTCAGATTGCGTTCAGTTACATGTGATGACTAA
```

Figure 13

MAGRRLTWISEFIVGALDSDKYPLVKWLDRSTGTFLAPAARNDVIPLDSLQFFID
FKRECLSKGLHPRDLLGSPITAFGKICTTSRRLRRLPGEEYEVVQGINCRRWRLL
CAEVKECWWCVHARTHLHSGSSLWEILYQHSVRLEKHRRRPRRPFVGENSDSSE
EDHPAFCDVPVTQTGAESEDSGDEGPSTRHSASGVQPVDDANADSPGSGDEGPS
TRHSDSQPPPADETTVHTDNVEDDLTLLDKESACALMYHVGQEMDMLMRAM
CDEDLFDLLGIPEDVIATSQPGGDTDASGVVTEGSIAASAVGAGVEDVYLAGAL
EAQNVAGEYVLEISDEEVDDGAGLPPASRRRPVVGEFLWDDGPRRHERPTTRRI
RHRKLRSAYYRVARPPVMITDRLGVEVFYFGRPAMSLEVERKVFILCSQNPLADI
SHSCLHSRKGLRVLLPKPDDNNTGPGDVNLLAAVLRSFASGLVIVSLRSGIYVKN
LCKSTVLYHGNNPPKKFGVICGLSSRAVLDVFNVAQYRIQGHEHIKKTTVFIGGD
PTSAEQFDMVPLVIKLRLRSVTCDD

Figure 14

CATAATCGAGAACCTGAAGGGTCCCGGTACGCGTCCCTGTTTCTGGGCCGCC
GGCCGTCGCCTGAATATGACTCGGATCACTATCCAGTCATTTTGCACATTTA
CCTTGCCCCATTTTACCACAGAGACTAAAATTTTGACAAGTCTTCTTGTCACT
CTGTCCGGGTACCTCCCTTTGTCTTACCGCCCTCCGTTTTGCACTATAAATAT
CATTGCCGTTAGAAACCAGGCTCTATCCGCAACTTCTATGTTTCCTGTTATAG
TAGGCCCATGTGGGCTTGGGAGTGGCCAAACTCACTGAGTGGGACATCATTA
AAGGTTAGCGCCACCGTGTGGCTGCAAAATAAAGTCTGAGTGGTTATTTTTT
TCCTAGGCGGTTGGGATTCACTCAGCTGCCAAGGCAAGGGGGTGTCCCCTGC
AATGCAAGGTAATGAGGTTAGTAAAGTAAGACAAACATGTGGGCTTCATTAT
GCATGCAATACCCTGTTTCAAAGCTGGTCCGGGGCAGCATCACCCCAGATGT
TCTTGCCAGCGCTGGAGAGCACGATTCATAGTGAGAAACACATGTGTCTAAT
ACAGGCAATGCTTTTTGACCCGTGACTGAAGGTTAAAGCTGCAGGAAGCATG
TTGTGGTTTGCGTAGTAGATTACTTCTGTTGAGGTGGGGTAATGCTCGGAGG
CAGACCATTCTGACAGGTCAAC

SEQUENCE LISTING

<160> NUMBER OF SEQ ID NOS: 3

<210> SEQ ID NO 1
<211> LENGTH: 1704
<212> TYPE: DNA
<213> ORGANISM: Kaposi's sarcoma-associated herpesvirus

<400> SEQUENCE: 1

```
atggcgggac gcaggcttac ctggatttct gagtttattg taggtgcttt ggactctgat      60
aaatatcctt tggtcaagtg gctagataga tctactggaa catttcttgc tccggctgcc     120
cgtaatgacg taattcctct ggatagccta cagttttttca ttgattttaa gagggaatgc     180
```

-continued

```
ctatcgaagg gcctgcatcc cagagattta ctgggctcgc cgattacggc ttttgggaaa      240
atatgtacca cgtcgcggcg ccttagacgc ttgccaggtg aagagtacga ggtcgtacag      300
ggaattaatt gtagaaggtg cgcctcctg tgtgccgagg taaaggaatg ctggtggtgc       360
gttcatgcca ggactcacct acacagtggg tcatcactat gggaaatttt gtatcaacac      420
agtgtacggc tcgagaagca tcggagaaga ccaaggaggc catttgtggg tgaaaactcg      480
gattccagtg aggaggatca cccagccttt tgcgatgtgc cggtcacgca gacgggcgcg      540
gaatctgagg actctggaga cgagggacca tcgacgcgcc atagtgcgtc tggggttcag      600
ccagttgatg atgccaatgc cgactctcct ggctctggag acgaaggacc ctcgacgcgt      660
catagcgact cgcagccccc cccggccgat gaaacaacgg tgcacacaga caacgttgaa      720
gatgacctca cactgcttga taaagaatct gcatgtgcat tgatgtacca cgtgggacag      780
gagatggaca tgctaatgag ggcgatgtgc gatgaagacc tctttgatct gcttggcatc      840
ccagaggatg ttatcgcaac atcacagccc ggaggcgaca cggatgcaag cggcgtggta      900
acagagggct caatcgccgc ctcggctgtc ggggcgggtg tagaggatgt gtacttagct      960
ggggcactcg aggcccagaa tgtagcaggg gaatatgtgt tggagataag tgacgaagaa     1020
gtcgatgatg gtgctggact gccgccggcg tccagacgcc ggccagttgt tggcgaattt     1080
ttatgggatg atgggccacg gagacacgag aggcctacca cgaggcgcat cgccacagg      1140 aagcttagat ccgcatatta tagagtggca cggccgccag taatgataac cgataggctt     1200
ggtgtggaag tgttttattt tggccgccct gcaatgtctt tggaagtgga acgaaaggtg     1260
tttattctat gttcccagaa cccactggca gacattagcc actcttgctt gcattcgcgc     1320
aaagggttaa gagttttgtt gcccaaacct gacgacaata acacagggcc aggagacgtt     1380
aacctgctgg cggccgtgct gcgctcgttt gcttcgggtc ttgtgatagt ttctctccga     1440
tctggcattt atgttaagaa tttgtgcaag tctaccgtat tatatcatgg aaataatcct     1500
ccaaagaagt ttggtgtgat ctgcggactg tcatctaggg ctgttctgga tgttttaat    1560 gtggcacaat atcgcataca gggacatgag cacattaaaa aaacaactgt gttcatcgga     1620
ggtgacccaa cgtcggcaga acagttcgat atggtccccc tcgtcatcaa gctcagattg     1680
cgttcagtta catgtgatga ctaa                                            1704
```

<210> SEQ ID NO 2
<211> LENGTH: 567
<212> TYPE: PRT
<213> ORGANISM: Kaposi's sarcoma-associated herpesvirus

<400> SEQUENCE: 2

```
Met Ala Gly Arg Arg Leu Thr Trp Ile Ser Glu Phe Ile Val Gly Ala
 1               5                  10                  15

Leu Asp Ser Asp Lys Tyr Pro Leu Val Lys Trp Leu Asp Arg Ser Thr
            20                  25                  30

Gly Thr Phe Leu Ala Pro Ala Ala Arg Asn Asp Val Ile Pro Leu Asp
        35                  40                  45

Ser Leu Gln Phe Phe Ile Asp Phe Lys Arg Glu Cys Leu Ser Lys Gly
    50                  55                  60

Leu His Pro Arg Asp Leu Leu Gly Ser Pro Ile Thr Ala Phe Gly Lys
65                  70                  75                  80

Ile Cys Thr Thr Ser Arg Arg Leu Arg Arg Leu Pro Gly Glu Glu Tyr
                85                  90                  95

Glu Val Val Gln Gly Ile Asn Cys Arg Arg Trp Arg Leu Leu Cys Ala
```

-continued

```
                100                 105                 110
Glu Val Lys Glu Cys Trp Trp Cys Val His Ala Arg Thr His Leu His
            115                 120                 125
Ser Gly Ser Ser Leu Trp Glu Ile Leu Tyr Gln His Ser Val Arg Leu
        130                 135                 140
Glu Lys His Arg Arg Pro Arg Pro Phe Val Gly Glu Asn Ser
145                 150                 155                 160
Asp Ser Ser Glu Glu Asp His Pro Ala Phe Cys Asp Val Pro Val Thr
                165                 170                 175
Gln Thr Gly Ala Glu Ser Glu Asp Ser Gly Asp Glu Gly Pro Ser Thr
            180                 185                 190
Arg His Ser Ala Ser Gly Val Gln Pro Val Asp Asp Ala Asn Ala Asp
        195                 200                 205
Ser Pro Gly Ser Gly Asp Glu Gly Pro Ser Thr Arg His Ser Asp Ser
    210                 215                 220
Gln Pro Pro Ala Asp Glu Thr Thr Val His Thr Asp Asn Val Glu
225                 230                 235                 240
Asp Asp Leu Thr Leu Leu Asp Lys Glu Ser Ala Cys Ala Leu Met Tyr
                245                 250                 255
His Val Gly Gln Glu Met Asp Met Leu Met Arg Ala Met Cys Asp Glu
            260                 265                 270
Asp Leu Phe Asp Leu Leu Gly Ile Pro Glu Asp Val Ile Ala Thr Ser
        275                 280                 285
Gln Pro Gly Gly Asp Thr Asp Ala Ser Gly Val Val Thr Glu Gly Ser
    290                 295                 300
Ile Ala Ala Ser Ala Val Gly Ala Gly Val Glu Asp Val Tyr Leu Ala
305                 310                 315                 320
Gly Ala Leu Glu Ala Gln Asn Val Ala Gly Glu Tyr Val Leu Glu Ile
                325                 330                 335
Ser Asp Glu Glu Val Asp Asp Gly Ala Gly Leu Pro Pro Ala Ser Arg
            340                 345                 350
Arg Arg Pro Val Val Gly Glu Phe Leu Trp Asp Asp Gly Pro Arg Arg
        355                 360                 365
His Glu Arg Pro Thr Thr Arg Arg Ile Arg His Arg Lys Leu Arg Ser
    370                 375                 380
Ala Tyr Tyr Arg Val Ala Arg Pro Pro Val Met Ile Thr Asp Arg Leu
385                 390                 395                 400
Gly Val Glu Val Phe Tyr Phe Gly Arg Pro Ala Met Ser Leu Glu Val
                405                 410                 415
Glu Arg Lys Val Phe Ile Leu Cys Ser Gln Asn Pro Leu Ala Asp Ile
            420                 425                 430
Ser His Ser Cys Leu His Ser Arg Lys Gly Leu Arg Val Leu Leu Pro
        435                 440                 445
Lys Pro Asp Asp Asn Asn Thr Gly Pro Gly Asp Val Asn Leu Leu Ala
    450                 455                 460
Ala Val Leu Arg Ser Phe Ala Ser Gly Leu Val Ile Val Ser Leu Arg
465                 470                 475                 480
Ser Gly Ile Tyr Val Lys Asn Leu Cys Lys Ser Thr Val Leu Tyr His
                485                 490                 495
Gly Asn Asn Pro Pro Lys Lys Phe Gly Val Ile Cys Gly Leu Ser Ser
            500                 505                 510
Arg Ala Val Leu Asp Val Phe Asn Val Ala Gln Tyr Arg Ile Gln Gly
        515                 520                 525
```

-continued

```
His Glu His Ile Lys Lys Thr Thr Val Phe Ile Gly Gly Asp Pro Thr
    530                 535                 540

Ser Ala Glu Gln Phe Asp Met Val Pro Leu Val Ile Lys Leu Arg Leu
545                 550                 555                 560

Arg Ser Val Thr Cys Asp Asp
                565

<210> SEQ ID NO 3
<211> LENGTH: 648
<212> TYPE: DNA
<213> ORGANISM: Kaposi's sarcoma-associated herpesvirus

<400> SEQUENCE: 3
cataatcgag aacctgaagg gtcccggtac gcgtccctgt ttctgggccg ccggccgtcg      60
cctgaatatg actcggatca ctatccagtc attttgcaca tttaccttgc cccattttac    120
cacagagact aaaattttga caagtcttct tgtcactcat tgccgttaga aaccaggctc    180
tatccgcaac ttctatgttt cctgttatag taggcccatg tgggcttggg agtggccaaa    240
ctcactgagt gggacatcat taaaggttag cgccaccgtg tggctgcaaa ataaagtctg    300
agtggttatt tttttcctag gcggttggga ttcactcagc tgccaaggca aggggggtgtc   360 ccctgcaatg caaggtaatg aggttagtaa agtaagacaa acatgtgggc ttcattatgc    420
atgcaatacc ctgtttcaaa gctggtccgg ggcagcatca ccccagatct tcttgccagc    480
gctggagagc acgattcata gtgagaaaca catgtgtcta atacaggcaa tgcttttga    540 cccgtgactg aaggttaaag ctgcaggaag catgttgtgg tttgcgtagt agattacttc    600
tgttgaggtg gggtaatgct cggaggcaga ccattctgac aggtcaac                  648
```

SPLICED GENE OF KSHV / HHV8, ITS PROMOTER AND MONOCLONAL ANTIBODIES SPECIFIC FOR LANA2

The invention described herein was made with Government support under grant number R01 CA67391 from the National Cancer Institute. Accordingly, the United States Government has certain rights in this invention.

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

Kaposi's sarcoma-associated herpesvirus (KSHV) or human herpesvirus 8 (HHV8) is the most recently described DNA tumor virus. It is the infectious trigger for Kaposi's sarcoma, body cavity-based primary effusion lymphomas (PEL), and some subtypes of multicentric Castleman's disease (CD) for review see (37), KSHV-related CD is a polyclonal B cell hyperplasia that is presumably driven by KSHV vIL-6 secretion as well as other viral proteins. In contrast, PEL are B cell lymphomas that generally have a monoclonal origin as determined by immunoglobulin gene rearrangement and viral terminal repeat analyses (7, 20, 36). Terminal repeat analyses by Judde and colleagues (20) have also demonstrated that KS tumors can have an oligo- or monoclonal pattern, and may evolve from a polyclonal hyperplasia into a monoclonal tumor. Thus, KSHV may contribute to cell proliferation through secretion of viral cytokines and induction of cellular cytokines as in the case of CD, as well as through expression of transforming viral oncogenes, particularly in the case of PEL.

The KSHV genome has significant sequence homology to all classes of herpesviruses, but is unique among the human herpesviruses in encoding an extensive number of regulatory genes which have been pirated from the host genome during its evolution (30, 36). While a number of these genes have homology to known cellular oncogenes or transform rodent cell lines in vitro (2, 14, 26), only a small number of KSHV genes are routinely found to be expressed in tumor tissues. vBCL-2, vIRF1, vGPCR, and K01 are examples of KSHV proteins which might contribute to cell transformation in vitro but are not appreciably expressed in most KSHV-infected KS or PEL tumors (21, 24, 32, 38).

KSHV infected PEL cell lines constitutively express three viral genes, vFLIP (ORFK13), vCYC (ORF72), and LANA1 (ORF73), which are not inducible by tetradecanoyl phorbol acetate (TPA) or inhibited by phosphonoformic acid (PFA) and thus are unambiguously designated as latent or class I genes. These three proteins are transcribed on the major polycistronic latent transcripts, LT1 and LT2 (10, 39, 42). In vitro studies demonstrate that the viral cyclin associates with cyclin dependent kinase (CDK) 4 and 6, and phosphorylates pRB (8, 16, 28). LANA1 is believed to bind to the origin of replication to tether the viral genome to host chromatin during mitosis, effecting equal segregation of viral genome during division (3). LANA1 also binds to p53 and inhibits p53-mediated transcriptional activity and apoptosis (13). vCYC over-expression induces apoptosis (31) and it is at least theoretically possible that this may be inhibited in situ by the anti-apoptotic activities of other latency expressed proteins, such as vFLIP and LANA1.

Viral protein expression is highly restricted in KS and PEL tumors. Presently, only LANA1 protein has been shown by immunohistochemistry to be expressed in situ in all cells infected by KSHV (11, 22, 32). Viral cyclin and ORFK12 transcripts have been identified by in situ hybridization in all KSHV infected cells (9, 34), however, protein localization has yet to be performed. No other viral proteins examined thus far, including vIL-6 (K2), minor capsid protein (ORF26), K8, K8.1, vIRF1 (K9), K10, k11, PF-8 (ORF59), and ORF65 have a similar in situ constitutive pattern of expression (21, 32).

KSHV gene expression studies remain controversial. Since PEL cell lines can be manipulated into lytic replication by TPA and butyrate, studies on cultured cell lines have been used to classify KSHV genes into mutually-exclusive latent and lytic classes based on transcription kinetics (40). Frequently, KSHV expression patterns from cultured cell studies are assumed to be similar in tumor tissues in situ without direct evidence. However, a number of KSHV genes are expressed at low levels in resting PEL cell lines but are induced to high expression levels during TPA treatment and thus have properties of both latent and lytic genes (analogous to the EBV LMP1 expression pattern). This pattern of gene expression has been referred to as class II expression (37). Recent studies demonstrate that extension of results from expression studies in tissue culture cannot be uniformly applied to human tumor tissues in part because KSHV may have tissue-specific gene expression patterns. vIL-6, for example, behaves as a class II protein in tissue culture cell lines and is expressed in hematopoietic-derived cells but generally not in KS lesions (29). Thus, determining precisely which viral genes are likely to play a role in KSHV-related pathogenesis requires direct tissue examination of each tumor type. Discovery of additional genes that are constitutively expressed in KSHV-induced disorders is particularly important since these genes are likely to play a role in cell growth dysregulation.

For these reasons, discovery of a KSHV gene having a tissue-specific expression profile is important, particularly if the encoded protein is functionally capable of contributing to cell proliferation. In this paper we describe a new KSHV gene (K10.5) expressed in KSHV-infected hematopoietic tissues. This gene is located in a region containing a cluster of viral sequences with limited homology to the interferon regulatory factor (IRF) family of proteins (36). vIRF1 is encoded by ORF K9 and inhibits interferon-induced transcription and fully transforms NIH3T3 cells (12, 14, 27, 44). vIRF1 binds to histone acetyltransferase transcriptional coadaptors (5, 19) and induces cell transformation by activating the cMYC oncogene through an interferon-stimulated response element (ISRE) called the PRF element (19). Based on these findings and the fact that other tumor viruses target the same tumor suppressor pathways as KSHV, Jayachandra et al. found that both Epstein-Barr virus (EBV or HHV4) EBNA2 and adenovirus E1A proteins also activate cMYC but use differing sets of coadaptors from those used by vIRF1 (19). vIRF1 additionally inhibits p53- and Fas-induced apoptosis ((5) and unpublished obs, S. Jayachandra, P. S. Moore, Y. Chang). vIRF1, however, is not generally expressed in PEL or KS and is therefore unlikely to contribute to these diseases although it may be important in the pathogenesis of CD (21, 32). Another IRF-like KSHV open reading frame encoding vIRF2 and having NF-kB-inhibitory activity has been described (6). We show here that LANA2 is a B-cell specific factor that antagonizes p53 tumor suppressor functions and is expressed during latency.

KSHV/HHV8 is associated with three proliferative diseases ranging from viral cytokine-induced hyperplasia to monoclonal neoplasia: multicentric Castleman's disease (CD), Kaposi's sarcoma (KS), and primary effusion lymphoma (PEL). Here we report a new latency-associated 1704 bp KSHV spliced gene belonging to a cluster of KSHV sequences having homology to the interferon regulatory factor (IRF) family of transcription factors. ORFK10.5 encodes a protein, latency-associated nuclear antigen 2 (LANA2), which is expressed in KSHV-infected hematopoietic tissues including PEL and CD, but not KS lesions. LANA2 is abundantly expressed in the nuclei of cultured KSHV infected B-cells. Transcription of K10.5 in PEL cell cultures is not inhibited by DNA polymerase inhibitors nor significantly induced by phorbol ester treatment. Unlike LANA1, LANA2 does not elicit a serologic response from patients with KS, PEL or CD as measured by Western-blot hybridization. Both KSHV vIRF1 (ORFK9) and LANA2 (ORFK10.5) appear to have arisen through gene duplication of a captured cellular IRF gene. LANA2 is a potent inhibitor of p53-induced transcription in reporter assays. LANA2 antagonizes apoptosis due to p53 overexpression in p53-null SAOS-2 cells and apoptosis due to doxorubicin treatment of wild-type p53 U20S cells. While LANA2 specifically interacts with aminoacids 290–393 of p53 in glutathione-S-transferase pull-down assays, we were unable to demonstrate LANA2-p53 interaction in vivo by immunoprecipitation. These findings show that KSHV has tissue-specific latent gene expression programs and identify a new latent protein which may contribute to KSHV tumorigenesis in hematopoietic tissues via p53 inhibition.

SUMMARY OF THE INVENTION

This invention provides an isolated nucleic acid which encodes a Kaposi's sarcoma-associated herpesvirus latency-associated nuclear antigen 2 polypeptide (LANA2) or a fragment thereof.

This invention provides a replicable vector which comprises the isolated nucleic acid which encodes a Kaposi's sarcoma-associated herpesvirus latency-associated nuclear antigen 2 polypeptide.

This invention provides a host vector system which comprises the above vector and a suitable host cell. In one embodiment of the above host vector system, the host cell includes but is not limited to a eukaryotic cell, a hematopoietic cell, a B cell, a bacterial cell and E. Coli.

This invention provides a method of producing a polypeptide which comprises growing the above host vector system under suitable conditions permitting production of the polypeptide and recovering the polypeptide so produced.

This invention further provides an isolated nucleic acid comprising consecutive nucleotides having the sequence of a promoter of Kaposi's sarcoma-associated herpesvirus latency-associated nuclear antigen 2 transcription.

This invention provides a replicable vector which comprises the isolated nucleic acid comprising consecutive nucleotides having the sequence of a promoter of latency-associated nuclear antigen 2 transcription operably linked to a second nucleic acid.

This invention provides a host vector system which comprises a replicable vector which comprises the nucleic acid comprising consecutive nucleotides having the sequence of a promoter of latency-associated nuclear antigen 2 transcription operably linked to a second nucleic acid and a suitable host cell.

This invention provides a method of producing a polypeptide which comprises growing the above host vector system under suitable conditions permitting production of the polypeptide and recovering the polypeptide so produced.

This invention provides an isolated nucleic acid capable of specifically hybridizing to the isolated nucleic acid which encodes a Kaposi's sarcoma-associated herpesvirus latency-associated nuclear antigen 2 polypeptide or a fragment thereof.

This invention provides a Kaposi's sarcoma-associated herpesvirus latency-associated nuclear antigen 2 polypeptide or a fragment thereof.

This invention also provides an antibody capable of specifically binding to the above polypeptide.

This invention provides a composition comprising the above antibody and an agent conjugated to the antibody.

This invention provides a method of determining whether a subject is afflicted with a disease associated with Kaposi's sarcoma-associated herpesvirus (KSHV) infection of a B cell which comprises: (a) obtaining a suitable sample from the subject; (b) contacting the suitable sample with a detectable antibody capable of binding to Kaposi's sarcoma-associated herpesvirus latency-associated nuclear antigen 2 polypeptide or a fragment thereof so as to form a complex between the antibody and any Kaposi's sarcoma-associated herpesvirus latency-associated nuclear antigen 2 polypeptide or a fragment thereof present in the sample;(c) removing any unbound antibody; and (d) detecting any antibody which is bound to any Kaposi's sarcoma-associated herpesvirus latency-associated nuclear antigen 2 polypeptide or a fragment thereof in the sample, wherein the presence of antibody indicates that the subject is afflicted with the disease associated with Kaposi's sarcoma-associated herpesvirus infection of a B cell.

This invention provides a method of determining whether a subject is afflicted with a disease associated with Kaposi's sarcoma-associated herpesvirus infection of a B cell which comprises:(a) obtaining a suitable sample from the subject; (b) immobilizing a capturing antibody wherein the capturing antibody is capable of binding to Kaposi's sarcoma-associated herpesvirus latency-associated nuclear antigen 2 to a support; (c) removing any unbound capturing antibody; (d) contacting the capturing antibody with the suitable sample so as to form a complex between the antibody and any Kaposi's sarcoma-associated herpesvirus latency-associated nuclear antigen 2 present in the sample; (e) removing any unbound sample; (f) contacting the complex obtained in step (d) with a detectable antibody of Kaposi's sarcoma-associated herpesvirus latency-associated nuclear antigen 2 polypeptide or a fragment thereof so as to form a complex between the detectable antibody and the complex; (g) removing any unbound detectable antibody; and (h) detecting any detectable antibody which is bound to the complex wherein the presence of detectable antibody indicates that the subject is afflicted with the disease associated with Kaposi's sarcoma-associated herpesvirus infection of a B cell.

This invention provides a method of determining whether a subject is infected with Kaposi's sarcoma-associated herpesvirus which comprises:(a) obtaining a suitable sample from the subject; (b) contacting the suitable sample with the detectable antibody of Kaposi's sarcoma-associated herpesvirus latency-associated nuclear antigen 2 polypeptide or a fragment thereof so as to form a complex between the antibody and any polypeptide or fragment thereof present in the sample;(c) removing any unbound antibody; and (d) detecting any antibody which is bound to any Kaposi's sarcoma-associated herpesvirus latency-associated nuclear antigen 2 polypeptide or fragment thereof in the sample, wherein the presence of antibody indicates that the subject is infected with Kaposi's sarcoma-associated herpesvirus.

This invention provides a method of determining whether a subject is infected with Kaposi's sarcoma-associated herpesvirus which comprises:(a) obtaining a suitable sample from the subject; (b) immobilizing a capturing antibody wherein the capturing antibody is capable of binding to polypeptide or fragment thereof to a support; (c) removing any unbound capturing antibody;(d) contacting the capturing antibody with the suitable sample so as to form a complex between the antibody and Kaposi's sarcoma-associated herpesvirus latency-associated nuclear antigen 2 polypeptide or fragment thereof present in the sample; (e) removing any unbound sample; (f) contacting the complex obtained in step (d) with the detectable antibody which is bound to Kaposi's sarcoma-associated herpesvirus latency-associated nuclear antigen 2 polypeptide or fragment thereof so as to form a complex between the detectable antibody and the complex; (g) removing any unbound detectable antibody; and (h) detecting any detectable antibody which is bound to the complex wherein the presence of detectable antibody indicates that the subject is infected with Kaposi's sarcoma-associated herpesvirus.

This invention provides a kit for diagnosing Kaposi's sarcoma-associated herpesvirus infection comprising the labeled antibody capable of specifically binding to the Kaposi's sarcoma-associated herpesvirus latency-associated nuclear antigen 2 polypeptide or fragment thereof.

This invention provides a method of inhibiting p53 mediated apoptosis of a cell which comprises introducing into the cell an effective amount of the replicable vector which comprises the isolated nucleic acid which encodes Kaposi's sarcoma-associated herpesvirus latency-associated nuclear antigen 2 polypeptide or fragment thereof, so as to thereby inhibit p53 mediated apostosis of the cell.

This invention provides a method of immortalizing a cell which comprises introducing into the cell an amount of the replicable vector which comprises the isolated nucleic acid which encodes Kaposi's sarcoma-associated herpesvirus latency-associated nuclear antigen 2 polypeptide or fragment thereof effective to inhibit p53 mediated apoptosis of the cell, so as to thereby immortalize the cell.

This invention provides a method of producing an antibody which comprises introducing into a cell an amount of the replicable vector which comprises the isolated nucleic acid which encodes Kaposi's sarcoma-associated herpesvirus latency-associated nuclear antigen 2 polypeptide effective to inhibit p53 mediated apoptosis of the cell producing the antibody and thereby immortalizing the cell, so as to thereby produce the antibody.

This invention provides a method of determining whether a subject is infected with Kaposi's sarcoma-associated herpesvirus which comprises: (a) obtaining a suitable sample from the subject; (b) contacting the suitable sample with a detectable nucleic acid capable of hybriding to a nucleic acid which encodes Kaposi's sarcoma-associated herpesvirus latency-associated nuclear antigen 2 polypeptide or fragment thereof under hybridizing conditions so as to form a complex between the detectable nucleic acid and any nucleic acid which encodes a Kaposi's sarcoma-associated herpesvirus latency-associated nuclear antigen 2 polypeptide or fragment thereof which is present in the sample; (c) removing any unbound detectable nucleic acid; and (d) detecting any detectable nucleic acid which is bound to the complex, wherein the presence of detectable nucleic acid indicates that the subject is infected with Kaposi's sarcoma-associated herpesvirus.

This invention provides a kit for diagnosing Kaposi's sarcoma-associated herpesvirus infection comprising a labeled nucleic acid which encodes a Kaposi's sarcoma-associated herpesvirus latency-associated nuclear antigen 2 polypeptide or fragment thereof.

This invention provides a transgenic non-human animal which has stably integrated into the genome of its germ cells or somatic cells an exogenous nucleic acid construct wherein the nucleic acid construct comprises a B-cell specific promoter of Kaposi's sarcoma-associated herpesvirus latency-associated nuclear antigen 2 operably linked to a second nucleic acid which encodes a gene of interest and is introduced into the transgenic non-human animal, or an ancestor, at an embryonic stage. In one embodiment of the above transgenic animal, the animal is a mammal.

This invention provides a method for evaluating in a non-human transgenic animal the potential therapeutic effect of an agent for treating Kaposi's sarcoma-associated herpesvirus infection in a human, which comprises: (a) providing an agent to a transgenic non-human animal whose cells comprise the nucleic acid which encodes a Kaposi's sarcoma-associated herpesvirus latency-associated nuclear antigen 2 polypeptide; and (b) determining the therapeutic effect of the agent on the transgenic non-human animal by monitoring Kaposi's sarcoma-associated herpesvirus latency-associated nuclear antigen 2 expression, wherein a decrease in Kaposi's sarcoma-associated herpesvirus latency-associated nuclear antigen 2 indicates that the agent would have a potential therapeutic effect on Kaposi's sarcoma-associated herpesvirus infection in a human. In one embodiment of the above method, the animal is a mammal.

This invention provides a method of treating Kaposi's sarcoma-associated herpesvirus infection in a subject, which comprises introducing into the subject's cells an effective amount of the nucleic acid capable of specifically hybridizing to the isolated nucleic acid which encodes Kaposi's sarcoma-associated latency-associated nuclear antigen 2 polypeptide or fragment thereof to hybridize to any of the above nucleic acid which is present in the subject's cells, so as to thereby treat Kaposi's sarcoma-associated herpesvirus infection.

This invention provides a method of treating Kaposi's sarcoma-associated herpesvirus infection in a subject, which comprises introducing into the subject's cells an effective amount of a nucleic acid capable of specifically hybridizing to an isolated nucleic acid comprising nucleotides having the sequence of a promoter of latency-associated nuclear antigen 2 transcription to hybridize to any of this nucleic acid which is present in the subject's cells, so as to thereby treat the subject.

This invention provides a composition comprising the antibody capable of specifically binding to the polypeptide encoded by the isolated nucleic acid which encodes Kaposi's sarcoma-associated latency-associated nuclear antigen 2 polypeptide and a carrier.

This invention provides a method of treating a subject infected with Kaposi's sarcoma-associated herpesvirus, which comprises administering to the subject an amount of the above composition under conditions such that the antibody binds to any LANA2 present in the subject, so as to thereby treat the subject.

This invention provides a composition comprising the polypeptide encoded by the isolated nucleic acid which encodes Kaposi's sarcoma-associated latency-associated nuclear antigen 2 polypeptide or fragment thereof and a carrier.

Figure 1:
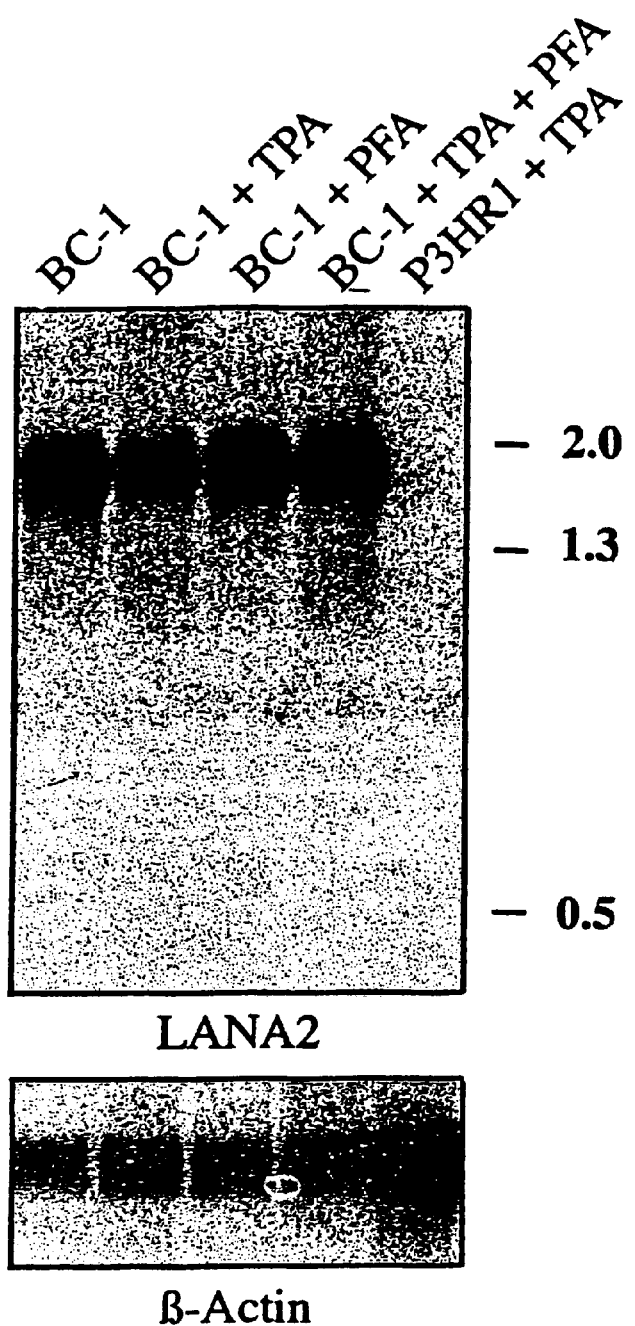
FIG. 1

Northern hybridization of BC-1 mRNA with ORF K10.5 probe. Probe hybridization for mRNA from uninduced BC-1 cells (lane 1), BC-1 cells treated with 20 ng/ml TPA for 48 hr (lane 2), BC-1 cells treated with 0.5 mM PFA (lane 3), BC-1 cells treated with both 20 ng/ml TPA and 0.5 mM PFA (lane 4), and KSHV-negative, EBV-infected P3HR1 cells treated with 20 ng/ml TPA (lane 5) are shown. Probe hybridizes to a 1.8 kb band which is not induced by TPA nor inhibited by PFA treatment, consistent with a latent pattern of viral gene transcription. Same blot is stripped and re-probed with b-actin as a control for loading.

FIG. 2

Transcript map of LANA2 in KSHV genomic environs showing V1 (vIRF1), V2, V3, and V4 probes used for northern blot hybridization. The V3 probe was used to screen a TPA-induced BC-1 cDNA library. Six phages (f672, f701, f702, f703, f731, 741) were isolated containing inserts of variable sizes. One full-length 1735 bp cDNA starting at nt 91,425 and terminating at nt 89,599 was identified and sequenced from phage f703. This cDNA contained a start ATG at position 91,393 and a splice donor/acceptor site corresponding to nt 90,938/90,837.

FIG. 3

Panel A. Comparison of motifs domains between IRF4/Pip and LANA2. IRF4 encodes a 450 aa protein with an N-terminal DNA-binding domain (DBD) defined by five tryptophan residues. This characteristic is not found in LANA2 (567 aa), however, a 213 bp region of LANA2, between amino acid 432 and 503, shows 32% amino acid identity with the C-terminal interaction domain (IAD) of IRF4.

Panel B. Phylogenetic tree for KSHV and human IRF proteins. LANA2 is most closely related to vIRF1 and vIRF2 suggesting a common origin from an ancestral IRF-like gene. Amino acid sequences were aligned using clustalW and the phylogenetic tree was generated using the Bootstrap NJ tree 1000 program. Protein peptides sources are as follows: hIRF1 [gi:87992], hIRF2 [gi:539621], hIRF3 [gi:4504725], hIRF4 [gi:2497445], hIRF5 [gi:4504727], hIRF6 [gi:3122293], hIRF7 [gi:4809288], ICSBP(hIRF8) [gi6016308], ISGF3 g [gi:266392], KSHV vIRF1 [gi:4929348], KSHV vIRF2 [3152728] and KSHV LANA2 [A4008303]. A phylogenetic tree comparing the IRF-like proteins from the RRV26-95 isolate and the KSHV IRF-like proteins has been published by Alexander et al (1).

FIG. 4

Cytospin preparation of TPA stimulated BCBL-1 cells immunostained with CM-10A2 mouse monoclonal antibody against LANA2. LANA2 demonstrates a finely speckled nuclear pattern exclusive of nucleolar zones in essentially all BCBL-1 cells (60× magnification, hematoxylin counterstain).

FIG. 5

Immunofluorescence double co-localization of LANA1 and LANA2 in KSHV infected BCBL-1 cells. Panel A shows LANA1 protein (red) in a coarsely speckled nuclear distribution, panel B demonstrates the diffuse, finely speckled nuclear pattern of LANA2 protein (green), and panel C shows double filter, co-localization of the two. Although some subnuclear regions show the distinct dispersal of the two proteins exclusive of each other, yellow nuclear staining is also evident in other areas possibly representing co-localization of a subfraction of LANA1 and LANA2. Cells undergoing mitosis (arrow) appear to express only LANA1 exclusive of LANA2 (panel C) (100×, Texas Red and FITC).

FIG. 6

Immunolocalization of LANA1 compared with LANA2 in KSHV-infected disorders. Panels A, B, and C represent LANA1 immunolocalization in a pericardial PEL infiltrating cardiac muscle, a germinal center from a lymph node with multicentric Castleman's disease and a cutaneous KS lesion biopsy, respectively. Adjacent sections of the same tissues are immunostained for LANA2 in panels D, E, and F. All tumor cells in PELs express both LANA1 (A) and LANA2 (D), and the majority of the KSHV-infected mantle zone lymphocytes in CD express both LANA1 (B) and LANA2 (E). However, while the majority of KS spindle cells express LANA1 (C), none express LANA2 (F).

FIG. 7

Immunolocalization of LANA1 (panel A) compared with LANA2 (panel B) in a lymph node with CD as well as KS. While the KS spindle cells (area within guide lines) and some of the mantle zone lymphocytes show strong nuclear positivity to LANA1, the adjacent section immunostained with LANA2 only shows this protein expressed in the lymphocyte subpopulation of KSHV infected cells in the mantle. The CD serves as an internal positive control for the negative LANA2 immunostaining of KS spindle cells.

FIG. 8

Inhibition of p53 transcriptional activity by LANA2. Representative luciferase assay showing inhibition of reporter gene expression by transient transfection of pcDNA.LANA2: A. SAOS-2 cells were transfected with 2 mg of plasmid pG13-Luc reporter plasmid together with 0.0 or 0.5 mg of pcDNA.p53 and 0.5 or 1 mg pcDNA.LANA2 as indicated. For control, SAOS-2 cells were transfected with the reporter plasmid pGL3-control and 0.0, 0.5 or 1 mg of pcDNA.LANA2. B. U20S cells were transfected with 2 mg of plasmid pG13Luc reporter plasmid with or without 0.5 or 1 mg pcDNA.LANA2 and treated with 0.4 mM Doxorubicin.

FIG. 9

In vitro GST pull down assays using [$^{35}$S]methionine labeled LANA2 or p53. LANA2 interacts with full length p53 protein as well as the p53 region between 290–393 aa

FIG. 10

LANA2 inhibits p53-induced apoptosis. SAOS-2 cells were transfected with pEGFP-F* and the empty expression vector pCDNA3.1 (A), pCDNA.p53 (B) or pCDNA.p53 and pCDNA.LANA2(C). Total DNA in all transfections was normalized using empty expression vector. After 48 h, cells were fixed and stained with propidium iodide. Cellular DNA content was analyzed by flow cytometry. U20S cells were transfected with pEGFP-F* and the empty expression vector pcDNA (D and E) or pcDNA.LANA2 (F). 18 h after transfection cells were treated with doxorubicin (0.4 uM) (E and F) and the cells were processed for DNA content analysis 30 h post treatment. Numbers indicate the percentage of cells in the sub-G1 phase of the cell cycle.

FIG. 11

Negative sero-reactivity to LANA2 in patients with KS, PEL, and MCD. LANA2 expressed in COS7 cells failed to react on western blotting with serum from patients with various KSHV-related disorders. None of 14 sera from individuals with AIDS-KS (n=4), classical KS (n=4), KSHV seropositive Castleman's disease (n=4) or PEL (n=2) showed serologic reactivity to LANA2. Negative control sera from four blood donors (seronegative for ORF65 and LANA1 antigens) were also non-reactive, whereas the supernatants from two mouse monoclonal LANA2 hybridoma clones (CM-10A2 and CM-8B6) were positive. "*" denotes clones CM-10A2 and CM-8B6.

FIG. 12

Kaposi's sarcoma-associated herpesvirus latency-associated nuclear antigen 2 (LANA2) nucleic acid sequence (SEQ ID NO: 1).

FIG. 13

Kaposi's sarcoma-associated herpesvirus latency-associated nuclear antigen 2 (LANA2) polypeptide sequence (SEQ ID NO: 2).

FIG. 14

Kaposi's sarcoma-associated herpesvirus latency-associated nuclear antigen 2 (LANA2) promoter nucleic acid sequence (SEQ ID NO: 3).

DETAILED DESCRIPTION OF THE INVENTION

As used herein, the following standard abbreviations are used throughout the specification to indicate specific amino acids:

| | |
|---|---|
| A = ala = alanine | R = arg = arginine |
| N = asn = asparagine | D = asp = aspartic acid |
| C = cys = cysteine | Q = gln = glutamine |
| E = glu = glutamic acid | G = gly = glycine |
| H = his = histidine | I = ile = isoleucine |
| L = leu = leucine | K = lys = lysine |
| M = met = methionine | F = phe = phenylalanine |
| P = pro = proline | S = ser = serine |
| T = thr = threonine | W = trp = tryptophan |
| Y = tyr = tyrosine | V = val = valine |
| B = asx = asparagine or aspartic acid | |
| Z = glx = glutamine or glutamic acid | |

As used herein, the following standard abbreviations are used throughout the specification to indicate specific nucleotides: C=cytosine; A=adenosine; T=thymidine; G=guanosine; and U=uracil.

This invention provides an isolated nucleic acid which encodes a Kaposi's sarcoma-associated herpesvirus latency-associated nuclear antigen 2 polypeptide (LANA2) or a fragment thereof.

In one embodiment of the above nucleic acid, the polypeptide comprises consecutive amino acids having the amino acid sequence set forth in SEQ ID NO: 2. In a further embodiment of the above nucleic acid, the isolated nucleic acid is designated ORFK10.5 and comprises consecutive nucleotides having the sequence set forth in SEQ ID NO: 1.

As used herein, the term "nucleic acid" refers to either DNA or RNA, including complementary DNA (cDNA), genomic DNA and messenger RNA (mRNA). As used herein, "genomic" means both coding and non-coding regions of the isolated nucleic acid molecule. "Nucleic acid sequence" refers to a single- or double-stranded polymer of deoxyribonucleotide or ribonucleotide bases read from the 5' to the 3' end. It includes both replicating vectors, infectious polymers of DNA or RNA and nonfunctional DNA or RNA.

The nucleic acids of the subject invention also include nucleic acids coding for polypeptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the polypeptide) which share some or all of the properties of the naturally-occurring forms.

As used herein, the phrase "nucleic acid encoding" refers to a nucleic acid which directs the expression of a specific polypeptide. The nucleic acid sequences include both the DNA strand sequence that is transcribed into RNA, the complementary DNA strand, and the RNA sequence that is translated into protein. The nucleic acid includes both the full length nucleic acid sequence as well as non-full length sequences. It being further understood that the sequence includes the degenerate codons of the native sequence or sequences which may be introduced to provide codon preference in a specific host cell.

As used herein, "peptide" and "polypeptide" are used to denote two or more amino acids linked by a peptidic bond between the α-carboxyl group of one amino acid and the α-amino group of the next amino acid. Peptide includes not only the full-length protein, but also partial-length fragments. Peptides may be produced by solid-phase synthetic methods that are well-known to those skilled in the art. In addition to the above set of twenty-two amino acids that are used for protein synthesis in vivo, peptides may contain additional amino acids, including but not limited to hydroxyproline, sarcosine, and β-carboxyglutamate. The peptides may contain modifying groups including but not limited to sulfate and phosphate moieties. Peptides can be comprised of L- or D-amino acids, which are mirror-image forms with differing optical properties. Peptides containing D-amino acids have the advantage of being less susceptible to proteolysis in vivo.

Peptides may by synthesized in monomeric linear form, cyclized form or as oligomers such as branched multiple antigen peptide (MAP) dendrimers (Tam et al. Biopolymers 51:311, 1999). Nonlinear peptides may have increased binding affinity by virtue of their restricted conformations and/or oligomeric nature. Peptides may also be produced using recombinant methods as either isolated peptides or as a portion of a larger fusion protein that contains additional amino acid sequences.

Peptides may be chemically conjugated to proteins by a variety of well-known methods. Such peptide-protein conjugates can be formulated with a suitable adjuvant and administered parenterally for the purposes of generating polyclonal and monoclonal antibodies to the peptides of interest. Alternatively, unconjugated peptides can be formulated with adjuvant and administered to laboratory animals for the purposes of generating antibodies. Methods for generating and isolating such antibodies are well-known to those skilled in the art.

The nucleic acids of the subject invention include but are not limited to DNA, RNA, mRNA, synthetic DNA, genomic DNA, and cDNA.

In one embodiment, the above nucleic acid is detectable. In one embodiment of the above nucleic acid, the nucleic acid is labeled with a detectable marker. As used herein, "detectable marker" includes but is not limited to a radioactive label, or a calorimetric, a luminescent, or a fluorescent marker. As used herein, "labels" include radioactive isotopes, fluorescent groups and affinity moieties such as biotin that facilitate detection of the labeled peptide. Other labels and methods for attaching labels to compounds are well-known to those skilled in the art.

This invention provides a replicable vector which comprises the isolated nucleic acid which encodes a Kaposi's sarcoma-associated herpesvirus latency-associated nuclear antigen 2 polypeptide. In one embodiment, the above vector includes but is not limited to plasmid, cosmid, λ phage and YAC. As used herein, the term "vector" refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome (s). Where a vector is being maintained by a host cell, the vector may either be stably replicated by the cells during mitosis as an autonomous structure, or is incorporated within the host's genome.

This invention provides a host vector system which comprises the above vector and a suitable host cell. In one embodiment of the above host vector system, the host cell includes but is not limited to a eukaryotic cell, a hematopoietic cell, a B cell, a bacterial cell and E. Coli.

This invention provides a method of producing a polypeptide which comprises growing the above host vector system under suitable conditions permitting production of the polypeptide and recovering the polypeptide so produced.

This invention further provides an isolated nucleic acid comprising consecutive nucleotides having the sequence of a promoter of latency-associated nuclear antigen 2 transcription. In one embodiment of this nucleic acid, the nucleic acid comprises consecutive nucleotides having the sequence set forth in SEQ ID NO: 3. The promoter of the subject invention is capable of driving the expression of any gene in a B cell. Accordingly, this permits one skilled in the art to study gene expression in certain cells, such as B cells, since there will be expression of the protein in the B cell. In a transgenic animal, the gene would be expressed in the B cells of the animal.

This invention provides a replicable vector which comprises the isolated nucleic acid comprising consecutive nucleotides having the sequence of a promoter of latency-associated nuclear antigen 2 transcription operably linked to a second nucleic acid. This second nucleic acid is one which encodes a protein or gene of interest. As used herein, the term "operably linked" refers to linkage of a promoter upstream from a DNA sequence such that the promoter mediates transcription of the DNA sequence.

The vector of the subject invention includes but is not limited to a plasmid, cosmid, λ phage and YAC.

This invention provides a host vector system which comprises a replicable vector which comprises the nucleic acid comprising consecutive nucleotides having the sequence of a promoter of latency-associated nuclear antigen 2 transcription operably linked to a second nucleic acid and a suitable host cell. The host cell includes but is not limited to a eukaryotic cell, a hematopoietic cell, a B cell, a bacterial cell and E. Coli.

This invention provides a method of producing a polypeptide which comprises growing the above host vector system under suitable conditions permitting production of the polypeptide and recovering the polypeptide so produced.

This invention provides an isolated nucleic acid capable of specifically hybridizing to the isolated nucleic acid which encodes a Kaposi's sarcoma-associated herpesvirus latency-associated nuclear antigen 2 polypeptide or a fragment thereof. This invention also provides a nucleic acid capable of specifically hybridizing to the isolated nucleic acid comprising nucleotides having the sequence of a promoter of latency-associated nuclear antigen 2 transcription. The above nucleic acids include but are not limited to DNA, RNA, mRNA, synthetic DNA, genomic DNA, and cDNA. The phrase "specifically hybridizing" and the phrase "selectively hybridizing" describe a nucleic acid that hybridizes, duplexes or binds only to a particular target DNA or RNA sequence when the target sequences are present in a preparation of total cellular DNA or RNA. By selectively hybridizing it is meant that a nucleic acid binds to a given target in a manner that is detectable in a different manner from non-target sequence under high stringency conditions of hybridization. "Complementary", "antisense" or "target" nucleic acid sequences refer to those nucleic acid sequences which selectively and specifically hybridize to a nucleic acid. Proper annealing conditions depend, for example, upon a nucleic acid's length, base composition, and the number of mismatches and their position on the nucleic acid, and must often be determined empirically. For discussions of nucleic acid design and annealing conditions for hybridization, see, for example, Sambrook et al. (1989) *Molecular Cloning: A Laboratory Manual* (2nd ed.), Cold Spring Harbor Laboratory, Vols. 1–3 or Ausubel, F., et al. (1987) *Current Protocols in Molecular Biology,* New York. The above hybridizing nucleic acids may vary in length. The hybridizing nucleic acid length includes but is not limited to a nucleic acid of at least 15 nucleotides in length, of at least 25 nucleotides in length, or at least 50 nucleotides in length.

This invention provides a Kaposi's sarcoma-associated herpesvirus latency-associated nuclear antigen 2 polypeptide or a fragment thereof. This invention also provides a purified and/or an isolated polypeptide. In one embodiment of the above polypeptide, the nucleic acid comprises consecutive nucleotides having the sequence set forth in SEQ ID NO: 1. This invention provides an isolated polypeptide comprising consecutive amino acids having the amino acid sequence set forth in SEQ ID NO:2.

The phrase "isolated" or "purified" when referring to a polypeptide, means a composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

This invention also provides an antibody capable of specifically binding to the above polypeptide. The antibody includes but is not limited to a monoclonal antibody or a polyclonal antibody. The polyclonal and monoclonal antibodies of the invention are immunoreactive with the peptides or immunogenic fragments of the peptides or functionally capable of binding an epitopic determinant of the peptides.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

The phrase "specifically binding" refers to a binding reaction which is determinative of the presence of the LANA2 polypeptide of the invention in the presence of a heterogeneous population of polypeptides and other biologics including viruses other than KSHV. Thus, under designated immunoassay conditions, the specified antibodies bind to the LANA2 antigen and do not bind in a significant amount to other antigens present in the sample.

In one embodiment of the above antibody, the antibody is humanized. As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody, i.e., in the present invention, the ability to bind CCR5.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 (45) comprise the production of chimeric antibodies having a variable region of one antibody and a constant region of another antibody.

U.S. Pat. No. 5,225,539 (46) describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. No. 5,585,089 (47) and U.S. Pat. No. 5,693,761 (48) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 (49) also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 Å of the CDRs in a three dimensional model of the antibody and is predicted to be capable of interacting with the CDRs. The above methods are merely illustrative of some of the methods that one skilled in the art could employ to make humanized antibodies.

In one embodiment, the antibody of the subject invention is detectable. In one embodiment of the above antibody, the detectable antibody is labeled with a detectable marker as described above.

This invention provides a composition comprising the above antibody and an agent conjugated to the antibody. In one embodiment, the agent is a radioactive isotope or toxin.

This invention provides a method of determining whether a subject is afflicted with a disease associated with Kaposi's sarcoma-associated herpesvirus (KSHV) infection of a B cell which comprises: (a) obtaining a suitable sample from the subject; (b) contacting the suitable sample with a detectable antibody capable of binding to Kaposi's sarcoma-associated herpesvirus latency-associated nuclear antigen 2 polypeptide or a fragment thereof so as to form a complex between the antibody and any Kaposi's sarcoma-associated herpesvirus latency-associated nuclear antigen 2 polypeptide or a fragment thereof present in the sample; (c) removing any unbound antibody; and (d) detecting any antibody which is bound to any Kaposi's sarcoma-associated herpesvirus latency-associated nuclear antigen 2 polypeptide or a fragment thereof in the sample, wherein the presence of antibody indicates that the subject is afflicted with the disease associated with Kaposi's sarcoma-associated herpesvirus infection of a B cell.

This invention provides a method of determining whether a subject is afflicted with a disease associated with Kaposi's sarcoma-associated herpesvirus infection of a B cell which comprises:(a) obtaining a suitable sample from the subject; (b) immobilizing a capturing antibody wherein the capturing antibody is capable of binding to Kaposi's sarcoma-associated herpesvirus latency-associated nuclear antigen 2 to a support; (c) removing any unbound capturing antibody; (d) contacting the capturing antibody with the suitable sample so as to form a complex between the antibody and any Kaposi's sarcoma-associated herpesvirus latency-associated nuclear antigen 2 present in the sample; (e) removing any unbound sample; (f) contacting the complex obtained in step (d) with a detectable antibody of Kaposi's sarcoma-associated herpesvirus latency-associated nuclear antigen 2 polypeptide or a fragment thereof so as to form a complex between the detectable antibody and the complex; (g) removing any unbound detectable antibody; and (h) detecting any detectable antibody which is bound to the complex wherein the presence of detectable antibody indicates that the subject is afflicted with the disease associated with Kaposi's sarcoma-associated herpesvirus infection of a B cell.

The disease in the above methods includes but is not limited to Castleman's disease and Primary Effusion Lymphoma. The disease may also be one not associated with a B cell.

This invention provides a method of determining whether a subject is infected with Kaposi's sarcoma-associated herpesvirus which comprises:(a) obtaining a suitable sample from the subject; (b) contacting the suitable sample with the detectable antibody of Kaposi's sarcoma-associated herpesvirus latency-associated nuclear antigen 2 polypeptide or a fragment thereof so as to form a complex between the antibody and any polypeptide or fragment thereof present in the sample; (c) removing any unbound antibody; and (d) detecting any antibody which is bound to any Kaposi's sarcoma-associated herpesvirus latency-associated nuclear antigen 2 polypeptide or fragment thereof in the sample, wherein the presence of antibody indicates that the subject is infected with Kaposi's sarcoma-associated herpesvirus.

This invention provides a method of determining whether a subject is infected with Kaposi's sarcoma-associated herpesvirus which comprises:(a) obtaining a suitable sample from the subject; (b) immobilizing a capturing antibody wherein the capturing antibody is capable of binding to polypeptide or fragment thereof to a support; (c) removing any unbound capturing antibody;(d) contacting the capturing antibody with the suitable sample so as to form a complex between the antibody and Kaposi's sarcoma-associated herpesvirus latency-associated nuclear antigen 2 polypeptide or fragment thereof present in the sample; (e) removing any unbound sample; (f) contacting the complex obtained in step (d) with the detectable antibody which is bound to Kaposi's sarcoma-associated herpesvirus latency-associated nuclear antigen 2 polypeptide or fragment thereof so as to form a complex between the detectable antibody and the complex; (g) removing any unbound detectable antibody; and (h) detecting any detectable antibody which is bound to the complex wherein the presence of detectable antibody indicates that the subject is infected with Kaposi's sarcoma-associated herpesvirus.

The suitable sample includes but is not limited to tonsil tissue, lymph nodes, spleen, skin lesions, blood, serum, plasma, cerebrospinal fluid, lymphocytes, urine, transudates, exudates, bone marrow cells, or supernatant from a cell culture.

In one embodiment of the above method, the antigen bound by the antibody is detected by an immunoassay. The immunoassay of the above method includes but is not limited to ELISA, IFA, and Western blotting.

As used herein, "capturing antibody" refers to an antibody capable of binding a polypeptide, a second antibody or a complex comprising an antibody and a polypeptide as described above. In one embodiment, a capturing antibody binds to a different epitope on the target protein than the detecting antibody.

As used herein, "support" includes but is not limited to a solid surface, a bead, a column, a plastic dish, a plastic plate, a microscope slide, and a nylon membrane. The use of these and other supports are known by one skilled in the art.

This invention provides a kit for diagnosing Kaposi's sarcoma-associated herpesvirus infection comprising the labeled antibody capable of specifically binding to the Kaposi's sarcoma-associated herpesvirus latency-associated nuclear antigen 2 polypeptide or fragment thereof. In one embodiment of the above kit, the kit further comprises a means for determining the level of Kaposi's sarcoma-associated herpesvirus latency-associated nuclear antigen 2 polypeptide or fragment thereof bound by an antibody. In one embodiment of the above kit, the labeled antibody capable of specifically binding to the polypeptide encoded by the isolated nucleic acid of Kaposi's sarcoma-associated herpesvirus latency-associated nuclear antigen 2 polypeptide or fragment thereof is bound to a support.

Studies have shown that LANA2 polypeptide can inhibit p53 mediated apoptosis. Accordingly, this invention provides a method of inhibiting p53 mediated apoptosis of a cell which comprises introducing into the cell an effective amount of the replicable vector which comprises the isolated nucleic acid which encodes Kaposi's sarcoma-associated herpesvirus latency-associated nuclear antigen 2 polypeptide or fragment thereof, so as to thereby inhibit p53 mediated apostosis of the cell.

This invention provides a method of immortalizing a cell which comprises introducing into the cell an amount of the replicable vector which comprises the isolated nucleic acid which encodes Kaposi's sarcoma-associated herpesvirus latency-associated nuclear antigen 2 polypeptide or fragment thereof effective to inhibit p53 mediated apoptosis of the cell, so as to thereby immortalize the cell.

As used herein, "immortalizing" refers to the action of LANA2 polypeptide in a B cell wherein the LANA2 polypeptide interacts with the p53 mediated apoptosis pathway to inhibit the action of p53 in the cell. The above interaction does not allow the cell to die, thereby creating an "immortalized" cell.

This invention provides a method of producing an antibody which comprises introducing into a cell an amount of the replicable vector which comprises the isolated nucleic acid which encodes Kaposi's sarcoma-associated herpesvirus latency-associated nuclear antigen 2 polypeptide effective to inhibit p53 mediated apoptosis of the cell producing the antibody and thereby immortalizing the cell, so as to thereby produce the antibody. An application of this method is to immortalize a cell which produces an antibody so to thereby increase production of the antibody.

The cell in the above methods includes but is not limited to a hematopoietic tissue cell, and a B cell.

As used herein, the term "introducing into a cell" includes but is not limited to transduction and transfection. Transfection can be achieved by calcium phosphate co-precipitates, conventional mechanical procedures such as micro-injection, electroporation, insertion of a plasmid encased in liposomes, or virus vectors or any other method known to one skilled in the art. This invention provides an antibody produced by the above method.

This invention provides a method of determining whether a subject is infected with Kaposi's sarcoma-associated herpesvirus which comprises: (a) obtaining a suitable sample from the subject; (b) contacting the suitable sample with a detectable nucleic acid capable of hybridizing to a nucleic acid which encodes Kaposi's sarcoma-associated herpesvirus latency-associated nuclear antigen 2 polypeptide or fragment thereof under hybridizing conditions so as to form a complex between the detectable nucleic acid and any nucleic acid which encodes a Kaposi's sarcoma-associated herpesvirus latency-associated nuclear antigen 2 polypeptide or fragment thereof which is present in the sample; (c) removing any unbound detectable nucleic acid; and (d) detecting any detectable nucleic acid which is bound to the complex, wherein the presence of detectable nucleic acid indicates that the subject is infected with Kaposi's sarcoma-associated herpesvirus.

In one embodiment of the above method, the suitable sample includes but is not limited to tonsil tissue, lymph nodes, spleen, skin lesions, blood, serum, plasma, cerebrospinal fluid, lymphocytes, urine, transudates, exudates, bone marrow cells, or supernatant from a cell culture.

In one embodiment of the above methods, the subject is a mouse, rat, dog, guinea pig, ferret, rabbit, primate, and human. As used herein, "subject" means any animal or artificially modified animal capable of becoming KSHV infected. Artificially modified animals include, but are not limited to, SCID mice with human immune systems. The subjects include but are not limited to mice, rats, dogs, guinea pigs, ferrets, rabbits, and primates. In the preferred embodiment, the subject is a human being.

This invention provides a kit for diagnosing Kaposi's sarcoma-associated herpesvirus infection comprising a labeled nucleic acid which encodes a Kaposi's sarcoma-associated herpesvirus latency-associated nuclear antigen 2 polypeptide or fragment thereof. In one embodiment of the above kit, the kit further comprises a means for determining the level of sample bound to the above labeled nucleic acid. In one embodiment of the above kit, the above labeled nucleic acid is bound to a support.

This invention provides a transgenic non-human animal which has stably integrated into the genome of its germ cells or somatic cells an exogenous nucleic acid construct wherein the nucleic acid construct comprises a B-cell specific promoter of Kaposi's sarcoma-associated herpesvirus latency-associated nuclear antigen 2 operably linked to a second nucleic acid which encodes a gene of interest and is introduced into the transgenic non-human animal, or an ancestor, at an embryonic stage. In one embodiment of the above transgenic animal, the animal is a mammal. In one embodiment of the above transgenic animal, the non-human animal is a mouse, a rat, a sheep, a dog, a primate, or a reptile.

This invention provides a method for evaluating in a non-human transgenic animal the potential therapeutic effect of an agent for treating Kaposi's sarcoma-associated herpesvirus infection in a human, which comprises: (a) providing an agent to a transgenic non-human animal whose cells comprise the nucleic acid which encodes a Kaposi's sarcoma-associated herpesvirus latency-associated nuclear antigen 2 polypeptide; and (b) determining the therapeutic effect of the agent on the transgenic non-human animal by monitoring Kaposi's sarcoma-associated herpesvirus latency-associated nuclear antigen 2 expression, wherein a decrease in Kaposi's sarcoma-associated herpesvirus latency-associated nuclear antigen 2 indicates that the agent would have a potential therapeutic effect on Kaposi's sarcoma-associated herpesvirus infection in a human. In one embodiment of the above method, the animal is a mammal. In one embodiment of the above method, the non-human animal is a mouse, a rat, a sheep, a dog, a primate, or a reptile.

The following U.S. Patents are hereby incorporated by reference: U.S. Pat. No. 6,025,539, IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Pat. No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981,829, .DELTA.Nur77 transgenic mouse; U.S. Pat. No. 5,936,138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app.

The methods used for generating transgenic animals are well known to one of skill in the art. For example, one may use the manual entitled "Manipulating the Mouse Embryo" by Brigid Hogan et al. (Ed. Cold Spring Harbor Laboratory) 1986.

See for example, Leder and Stewart, U.S. Pat. No. 4,736,866 for methods for the production of a transgenic mouse.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mammal as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

The "transgenic non-human animals" of the invention may be produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. U.S.A. 82, 4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. U.S.A. 82, 6927–6931; Van der Putten, et al. (1985) Proc. Natl. Acad. Sci U.S.A. 82, 6148–6152). Transfection is easily and efficiently obtained by culturing the blastomeres on a monolayer of virus-producing cells (Van der Putten, supra; Stewart, et al. (1987) EMBO J. 6, 383–388). Alternatively, infection can be performed at a later stage. Virus or virus-producing cells can be injected into the blastocoele (Jahner, D., et al. (1982) Nature 298, 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) Nature 292, 154–156; Bradley, M. O., et al. (1984) Nature 309, 255–258; Gossler, et al. (1986) Proc. Natl. Acad. Sci U.S.A. 83, 9065–9069; and Robertson, et al. (1986) Nature 322, 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468–1474.

As used herein, a "transgene" is a DNA sequence introduced into the germline of a non-human animal by way of human intervention such as by way of the above described methods.

This invention provides a method of treating Kaposi's sarcoma-associated herpesvirus infection in a subject, which comprises introducing into the subject's cells an effective amount of the nucleic acid capable of specifically hybridizing to the isolated nucleic acid which encodes Kaposi's sarcoma-associated latency-associated nuclear antigen 2 polypeptide or fragment thereof to hybridize to any of the above nucleic acid which is present in the subject's cells, so as to thereby treat Kaposi's sarcoma-associated herpesvirus infection. An application of this method is to inhibit transcription of Kaposi's sarcoma-associated latency-associated nuclear antigen 2 polypeptide or fragment thereof, thereby treating the subject.

As used herein, "effective amount" means an amount in sufficient quantities to either treat the subject or prevent the subject from becoming infected with Kaposi's sarcoma-associated herpesvirus. A person of ordinary skill in the art can perform simple titration experiments to determine what amount is required to treat the subject.

The subject invention has various applications which includes KSHV treatment such as treating a subject who has become afflicted with KSHV. As used herein, "afflicted with the disease" means that the subject has at least one cell which has been infected by KSHV. As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with KSHV.

Another application of the subject invention is to prevent a subject from contracting KSHV. As used herein, "contracting KSHV" means becoming infected with KSHV, whose genetic information replicates in and/or incorporates into the host cells. Another application of the subject invention is to treat a subject who has become infected with KSHV.

As used herein, "KSHV infection" means the introduction of KSHV genetic information into a target cell, such as by fusion of the target cell membrane with KSHV or an KSHV envelope glycoprotein cell. The target cell may be a bodily cell of a subject. In the preferred embodiment, the target cell is a bodily cell from a human subject.

This invention provides a method of treating Kaposi's sarcoma-associated herpesvirus infection in a subject, which comprises introducing into the subject's cells an effective amount of a nucleic acid capable of specifically hybridizing to an isolated nucleic acid comprising nucleotides having the sequence of a promoter of latency-associated nuclear antigen 2 transcription to hybridize to any of this nucleic acid which is present in the subject's cells, so as to thereby treat the subject. An application of this method is to hybridize a nucleic acid to the above promoter, thereby inhibiting Kaposi's sarcoma-associated herpesvirus latency-associated nuclear antigen 2 polypeptide expression, thereby treating Kaposi's sarcoma-associated herpesvirus infection in the subject.

This invention provides a composition comprising the antibody capable of specifically binding to the polypeptide encoded by the isolated nucleic acid which encodes Kaposi's sarcoma-associated latency-associated nuclear antigen 2 polypeptide and a carrier.

As used herein, "carriers" include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like. The carriers include but are not limited to an aerosol, intranasal, oral or topical carrier. Carriers are well known to those skilled in the art.

As used herein, "composition" means a mixture. The compositions include but are not limited to those suitable for oral, rectal, intravaginal, topical, nasal, opthalmic, or parenteral administration to a subject. As used herein, "parenteral" includes but is not limited to subcutaneous, intravenous, intramuscular, or intrasternal injections or infusion techniques.

This invention provides a method of treating a subject infected with Kaposi's sarcoma-associated herpesvirus, which comprises administering to the subject an amount of the above composition under conditions such that the antibody binds to any LANA2 present in the subject, so as to thereby treat the subject.

This invention provides a composition comprising the polypeptide encoded by the isolated nucleic acid which encodes Kaposi's sarcoma-associated latency-associated nuclear antigen 2 polypeptide or fragment thereof and a carrier.

In one embodiment of the methods of this invention, the cell is present in a subject and the contacting is effected by administering the compound to the subject.

The subject invention has therapeutic applications. For example, one skilled in the art can target a latency associated gene, such as the gene which encodes the LANA2 polypeptide, so as to inactivate the gene and thereby treat the KSHV infection or other diseases associated with KSHV infection, such as the B-cell associated diseases Castleman's disease or Primary Effusion Lymphoma. One can use antisense technology in order to inhibit the expression of a gene, such as LANA2. One can also use monoclonal antibody technology so as to degrade or sequester the protein, such as the LANA2 protein.

This invention will be better understood from the Experimental Details that follow. However, one skilled in the art will readily appreciate that the specific methods and results discussed are merely illustrative of the invention as described more fully in the claims that follow thereafter.

Experimental Details

A. Materials and Methods

Cell Cultures

BC-1, BCP-1, BCBL-1, BJAB, Ramos, and P3HR1 (obtained from the American Type Culture Collection—ATCC) cells were maintained in 1640 RPMI (GibcoBRL, Gaithersburg, Md.) supplemented with 10–20% fetal bovine serum (GibcoBRL). SAOS-2, U2OS, COS7 cells (obtained from ATCC), and IRF1/2 (−/−) cells (a gift from T. Taniguchi (43)) were maintained in DMEM (GibcoBRL) with 10% fetal bovine serum. Induction of viral lytic replication and gene transcription was performed by treatment of cells with 20 ng/ml TPA (Sigma Chemical Co., St. Louis, Mo.). Cells were harvested 48 h after treatment. To inhibit viral DNA replication, PFA (Sigma) was added at a concentration of 0.5 mM either or in the presence of 20 mg/ml TPA for 48 h.

Northern Analysis

Total RNA was extracted by the RNAzol method (TelTest, Friendswood, Tex.) followed by mRNA selection using a PolyATract mRNA isolation kit (Promega, Madison, Wis.). Five hundred nanograms of the poly(A)-selected mRNA was loaded per lane on formaldehyde 1% agarose gel and transferred onto nylon membranes (GeneScreen, NEN Research Products, Boston, Mass.). The V1 probe consists of the entire K9 ORF (14). The V1 probe as well as V2, V3 and V4 probes derived from PCR products (see FIG. 2)

```
(V2F: 5'-GGGAATTCGATGCCTAAAGCCGGTGGC-3' and

V2R: 5'-TGCGGCCGCTCAAACCTCACACCCCCT-3';

V3F: 5'-GGGAATTCGATGTACCACGTGGGACAG- 3' and

V3R: 5'-TGCGGCCGCTTAGTCATCACATGTAAC-3';

V4F: 5'-GGGAATTCGATGCCTCGCTACACGGAG-3' and

V4R: 5'-GGGAATTCGCTACCTCTGGGCTTTTTT-3')
``` were labeled by random priming using synthetic hexanucleotide primers (RediPrime, DNA labeling system; Amersham International, Amersham, England) and [$^{32}$p]dCTP. Hybridization was performed in 5× SSC (1× SSC is 0.15 M NaCl plus 0.015 M sodium citrate)-50% formamide-5× Denhardt's solution-2% sodium dodecyl sulfate-10% dextran sulfate-100 mg of denatured sheared salmon sperm DNA per ml at 42° C. b-actin probe was used to standardize the amount of RNA loaded.

cDNA Library Screening cDNA phage libraries of TPA stimulated BC-1 cells were constructed and amplified in the ZAP Express™ vector according to the manufacturer's protocol (Stratagene, La Jolla, Calif.). 3.2×10$^5$ plaques were screened following manufacturer's suggested protocols with the V3 probe made from the V3F and V3R PCR primers (used in northern analysis, see above).

Plasmids pcDNA.LANA2 was obtained by excising full length LANA2 insert with EcoRI and NotI digestion from phagemid, pBK-CMV-LANA2 (f703 screened from cDNA library). This insert was then cloned in frame into EcoRI/NotI prepared pcDNAHis3.1B vector (Invitrogen, Carlsbad, Calif.). pMET7.LANA2 was constructed by digesting pBK-CMV-LANA2 with PstI and XbaI. The isolated insert was then cloned into PstI/XbaI prepared pMET7 mammalian expression vector (41). The fidelity of all cloning junctions was verified on an ABI 377 Sequenator (Applied Biosystems Inc., Foster City, Calif.) pG13-Luc, a reporter plasmid containing 13 tandem p53-response elements derived from the p21 promoter, was a gift from W. El-Deiry and B. Volgelstein (4). pGL-3 control (Promega, Madison, Wis.) was used as a control vector for luciferase transient transfection assays. GST-p53(full length (FL)) and the C-terminus fragment of p53 (GST-p53 (290–393)) plasmids were a gift from W. Gu (17). DNA sequences corresponding to the 1–100 and 100–290 aminoacids of human p53 were amplified by PCR and subcloned into pGEX-KG (18) to generate the protein expression plasmids GST-p53 (1–100) and GST-p53 (100–290). pcDNA.p53 expression plasmid was a gift of RT Hay (35). pEGFP-F* (gift of W. Jiang) expresses green fluorescent protein (GFP) and was used as a marker for pcDNA.LANA2 and/or pcDNA.p53 transfection to gate fluorescent cells by FACS. The plasmid containing the Gal-4 binding domain (Gal4-BD), PAS2-1, the Gal4-activation domain (Gal4-AD), pGAD424, as well as the plasmids containing the DNA-BD/murine p53 fusion protein PVA3 and the DNA-AD/murine p53 fusion protein pGADp53 and control plasmids pCL1, PLAM5', pGBT9 and pTD1 were obtained from Clontech (Clontech laboratories, Palo Alto, Calif.).

Reporter Assays

SAOS-2 or U2OS cells were seeded at a density of $5 \times 10^4$ cells per plate in six-well plates 1 day before transfection. Transient transfections with plasmid DNA were performed using Cell Phect (Pharmacia Biotech, Piscataway, N.J.). In all experiments, total amounts of transfected DNA were equalized between wells using empty pcDNA3.1HisC (Invitrogen). Cells were harvested and lysed, and luciferase activity was measured by using standard protocols after 48 hr. pcDNAHis3.1LacZ (Invitrogen) was used to normalize luciferase activity to transfection efficiency. In this way, reporter expression levels were normalized to the amount of transfected plasmid for each experimental condition. Each measurement was performed in triplicate, with experiments independently replicated at least three times. p53-null SAOS-2 cells were co-transfected with 2 mg pG13-Luc in the presence or absence of 0.5 mg pcDNA.p53 with or without pcDNA.LANA2 (0.5–1 mg). U2OS cells were co-transfected with 2 mg pG13-Luc in the presence or absence of pcDNA.LANA2 (0.5–1 mg/well) and treated with 0.4 mM doxorubicin (Sigma) 18 h post-transfection.

Fluorescence Activated Cell Sorter (FACS) Analysis $1 \times 10^6$ SAOS-2 cells were transfected (Cell Phect) with 1 mg of the GFP expressing plasmid, pEGFP-F*, in the presence of pcDNA.p53 (4.5 mg) and/or pcDNA.LANA2 (4.5 mg) or the empty expression vector. U2OS cells were transfected with 1 mg pEGFP-F* in the presence or absence of the expression vector pcDNA.LANA2 (4.5–9 mg) and treated with doxorubicin 18 h post-transfection. 48 h after transfection, cells were washed in PBS and fixed at 4° C. in 80% ethanol in PBS for 1 h. Cells were then washed three times with PBS and incubated for 30 min at 37° C. in 0.1% Triton X-100, 0.1% Tri-sodium citrate, 0.5 mg/ml RNaseA, and 50 mg/ml propidium iodide. The DNA content of cells gated for GFP expression was then analyzed using a FACScan flow cytometer.

Activation of Caspase-8

Caspase-8 activation was determined using the synthetic oligopeptide substrate Ac-LETD-AFC from Bio-Rad (Bio-Rad Laboratories, Hercules, Calif.), as described by the manufacturer and the samples were read on a Bio-Rad VersaFluor™ Fluorometer.

GST Pull Down Assays

GST in vitro binding assays were performed using in vitro translated [$S^{35}$] methionine-labeled LANA2 incubated with p53 GST fusion proteins (GST-p53 (FL), GST-p53 (1–100), GST-p53(100–290), GST-p53 (290–393), and GST alone. In vitro translated [$S^{35}$] methionine-labeled p53 was incubated with GST-LANA2 and GST alone.

Coimmunoprecipitation

LANA2 (20 mg of pcDNA.LANA2) and p53 (20 mg of pcDNA.p53) were expressed in SAOS-2 cells by co-transfection and were immunoprecipitated with anti-LANA2 CM-8B6 or CM-10A2 antibodies, or D0-1 (Santa Cruz Biotech, Santa Cruz, Calif.), Pab 1801 (Santa Cruz,), and Ab-1 (Oncogene, Cambridge, Mass.) anti-p53 antibodies. Protein complexes were resolved by SDS/10% PAGE and transferred onto nitrocellulose membrane. LANA2 was detected using CM-8B6, CM-10A2 and p53 was detected using D0-1, Pab 1801, Ab-1 by immunoblotting and enhanced chemiluminescence (ECL, Amersham, Piscataway, N.J.).

Immunohistochemistry of KSHV Infected Tissues and Controls

Glass slides were obtained with the Cytospin 3 apparatus (Shandon Lipshaw, Pittsburgh, Pa.) using 25,000 washed cells per spot. These cytospins were air-dried overnight, fixed in acetone for 4 minutes at room temperature, air-dried for 30 minutes and processed for immunohistochemistry. Ten KS skin lesions, 5 lymph nodes from patients with CD, and biopsies from two cases of PEL were investigated for protein expression of LANA2 by immunohistochemistry. One CD lymph node also contained KS. Control tissues were tonsil biopsies from KSHV negative children. Mouse monoclonal antibody, clone CM-10A2, was made against bacterially produced GST-LANA2 and was confirmed to be specific to the 80 kD LANA2 protein on western blot hybridization of KSHV-infected cell lysates (BC-1, BCBL-1, BCP-1) compared to KSHV-uninfected cell lysates (BJAB, P3HR1, Ramos). CM-10A2 was non-reactive to GST protein by both ELISA and western blot hybridization. The rabbit polyclonal antibody against LANA1, R UK163, was the kind gift of B. Chandran. Microwave-ethylenediaminetetraacetic acid (EDTA) pretreatment was required for antigen retrieval. Antibody binding was revealed using peroxidase-labeled goat anti-mouse antisera (DAKO, Glostrupp, Denmark) followed by tyramide amplification (DuPont/NEN, Boston, Mass.) Reactions were developed using diaminobenzidine (DAB; Sigma) or amino ethyl carbazole (AEC; DAKO) as chromogenic substrates, and sections were counterstained with hematoxylin. Antibodies to KSHV vIL-6 (cytoplasmic staining) and PF-8 (perinuclear staining) were used for comparative antibody controls for tissue staining (32). For fluorescence double-immunostaining with LANA1 and LANA2, fluorescein-isothiocyanate (FITC)-conjugated goat anti-mouse was used in combination with goat anti-rabbit antisera (Southern Biotechnology) followed by Avidin Texas Red (Vector Laboratories, Burlingame, Calif.).

Serologic Analysis

COS7 cells were plated at a density of $10^6$ cells per 90 mm plate one day prior to transfection. Transfections were performed (Cell Phect) using 6 mg of pMET7.LANA2 or pMET7 empty vector as control. Cells were harvested 48 hr post-transfection, placed in 500 ml lysis buffer, incubated on ice for 20 minutes, centrifuged, and resuspended in 200 ul nuclear extraction buffer (20 mM HEPES pH7.9, 0.4M NaCl, 1 mM EDTA, 1 mM DTT, 1 mM PMSF, 1 mM sodium vanadate, 1 ug/ml aprotinin, leupeptin and pepstatin). 15 ug of protein was loaded into a single well comb for western blot analysis by SDS/12.5% PAGE. After transferring onto nitrocellulose membrane, strips were cut and incubated in CM-10A2 primary antibody overnight. After washing, strips were incubated for one hour in anti-human IgG alkaline phosphatase conjugate secondary antibody (1:3500 dilution; Sigma).

Yeast Two-Hybrid Assay

LANA2 was fused either to GAL4-AD in the plasmid pGAD424 or to GAL4 DNA-binding domain (BD) in the plasmid pAS2-1. The plasmids containing the murine p53 fused to GAL4 AD or GAL4BD were provided by Clontech. The yeast strain Y-190 was used for this two hybrid assay. Plasmids are introduced into Y-190 by the standard lithium acetate transformation method. To test for potential protein—protein interaction, transformants were screened for growth in medium lacking histidine but in the presence of 15 mM 3-aminotriazol (3-AT) (His+phenotype) or assayed for b-galactosidase activity (blue phenotype) in the presence of X-Gal (5-bromo-4-chloro-3-indolyl-B-D-galactopyranoside).

B. Results

Identification of the K10.5 (LANA2) Transcript

ORF K10.5 was originally described as a sequence feature rather than an open reading frame in Russo et al.'s is conservative annotation of the BC-1 genome (36). This gene was one of four KSHV sequences showing limited homology to cellular IRFs. Neipel and colleagues subsequently annotated a theoretical ORF K10.1 based on their sequencing of the KSHV genome from a KS lesion (30). We therefore sought to directly determine whether the four IRF-like motifs, including the putative K10.1 gene, in the KSHV genomic sequence represent expressed gene products using TPA-induced and uninduced BC-1 cell mRNAs.

Four probes spanning nt 83,860–85,209 (V1 probe), nt 88,409–88,909 (V2 probe), nt 89,599–90,540 (V3 probe) and nt. 93,635–94,126 (V4 probe) were generated by PCR (see FIG. 2). V1 probe corresponds to the ORFK9 region-encoding vIRF and expression patterns for this probe matched those previously described (27, 29, 37) in that the 1.5 kb mRNA is weakly detected in unstimulated BC-1 cells and induced to high levels of expression after TPA treatment. While probes V2 and V4 (corresponding to the vIRF2 protein gene (6)) did not hybridize to detectable transcripts in unstimulated or stimulated BC-1 cells, the V3 probe corresponding to ORFK10.5 hybridized to a 1.8 kb transcript that was absent from the KSHV negative control cell line, P3HR1 (FIG. 1). Expression of the K10.5 transcript is not affected by TPA stimulation or phosphonoformic acid (PFA) inhibition thereby qualifying it as a latent transcript in BC-1 cells. Similar results were also obtained using BCBL-1 cells (data not shown).

Since the transcript size identified by the V3 probe is incompatible with the predicted transcript for putative ORFK10.5, we screened a cDNA library made from TPA-stimulated BC-1 cells to identify spliced transcripts. Of $3.2 \times 10^5$ plaques screened, six positive phages were found with inserts ranging between 503 bp and 1735 bp in length (FIG. 2). The clones were sequenced and one (f703) contained the full length cDNA transcript beginning 31 bp upstream from a putative start ATG (nt 91,393) and having a stop codon at nt 89,599. All six cDNAs have a 3' termination coordinate at nt 89,599. Conserved splice-donor sites (nt 90,938 and nt 90,847) are present in the f703 insert, but only one of the five other phage inserts extended through the 5' splice junction. Splicing results in a 1704 bp full length transcript for the newly annotated gene which is designated ORFK10.5 to distinguish it from the unspliced 3' exon previously designated K10.1 (FIG. 2, GenBank Accession No. A4008303). This ORF is composed of a novel 455 bp 5' exon that is joined to the 3' exon 1339 bp internally to and out of frame with the previously annotated ORF K10.1 predicted from the genome sequence analysis (30).

Figure 3A:
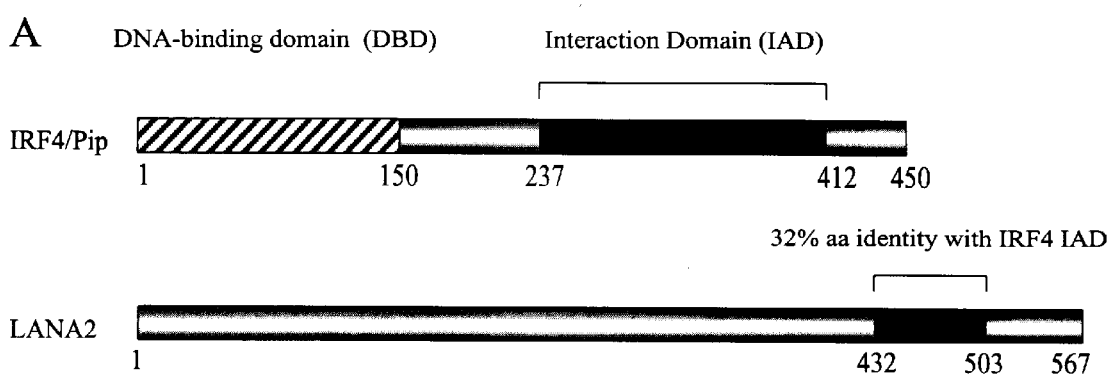
Figure 3B:
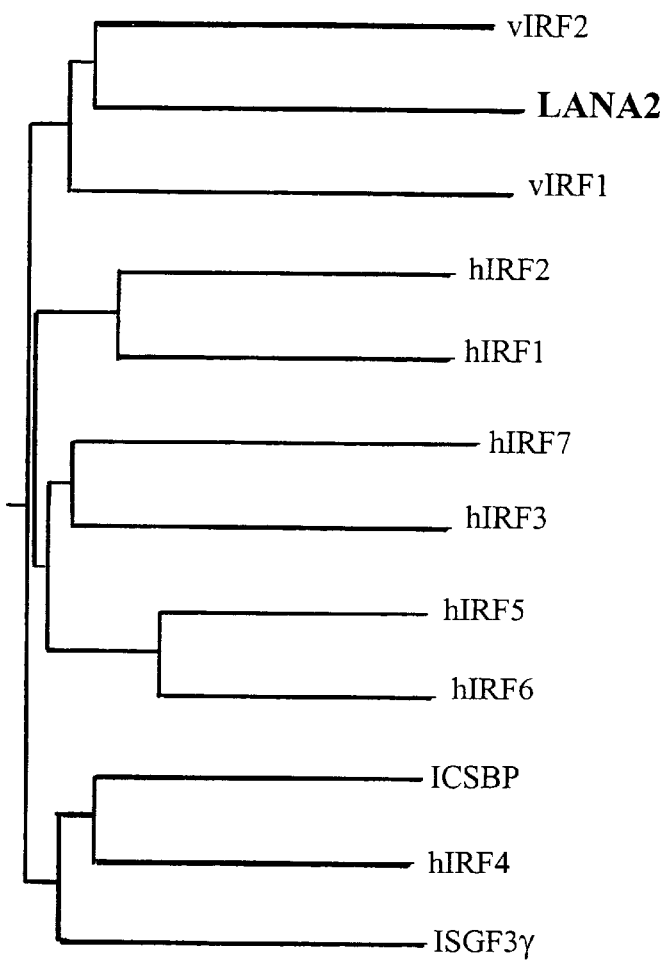

Based on its constitutive expression in BC-1 cells and its nuclear localization (see below), we refer to the protein encoded by ORFK10.5 as latency-associated nuclear antigen 2 (LANA2). LANA2 has low overall homology to members of the IRF family. Members of the IRF family of proteins have at least two common functional domains: an amino-terminal DNA binding domain (DBD) and a carboxyl-terminal activation domain. LANA2 does not have conserved tryptophans in its amino-terminus required for DNA-binding by IRF members, but has 32% amino acid identity over a 71 bp region corresponding to the IRF4 interaction domain (IAD) (FIG. 3A). Comparative phylogenetic analysis shows that the KSHV proteins vIRF1, vIRF2 and LANA2 have a common branch point and appear to have arisen through gene duplication of a captured ancestral IRF-like cellular gene (FIG. 3B). In a previous study from our laboratory surveying transcription of the KSHV genome in BC-1 cells (37), we failed to detect this transcript, possibly due to use of large probes covering this region which resulted in a low signal intensity on northern blotting.

LANA2 Expression in vitro and in vivo

Figure 4:
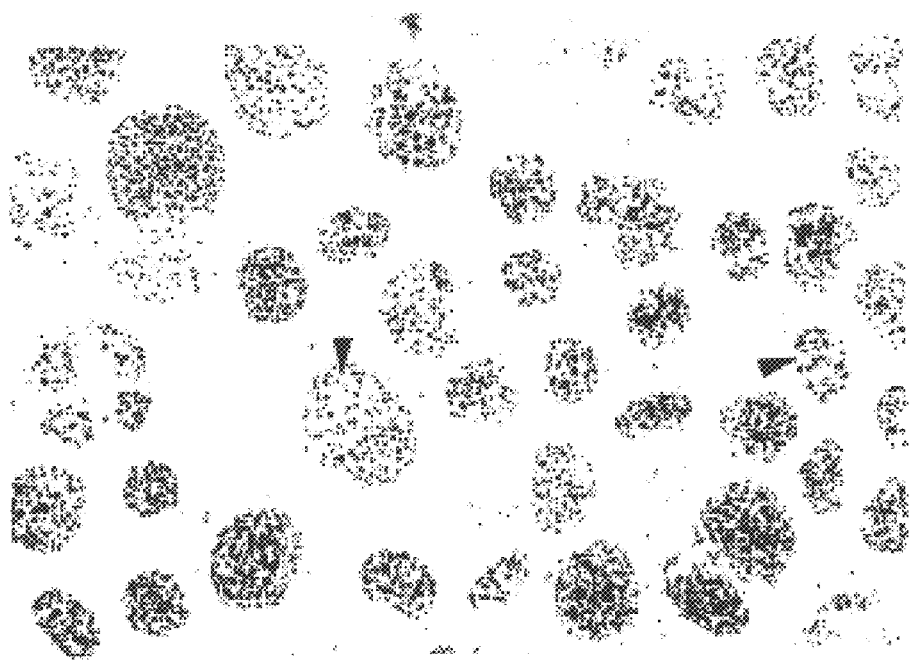
Figure 5:
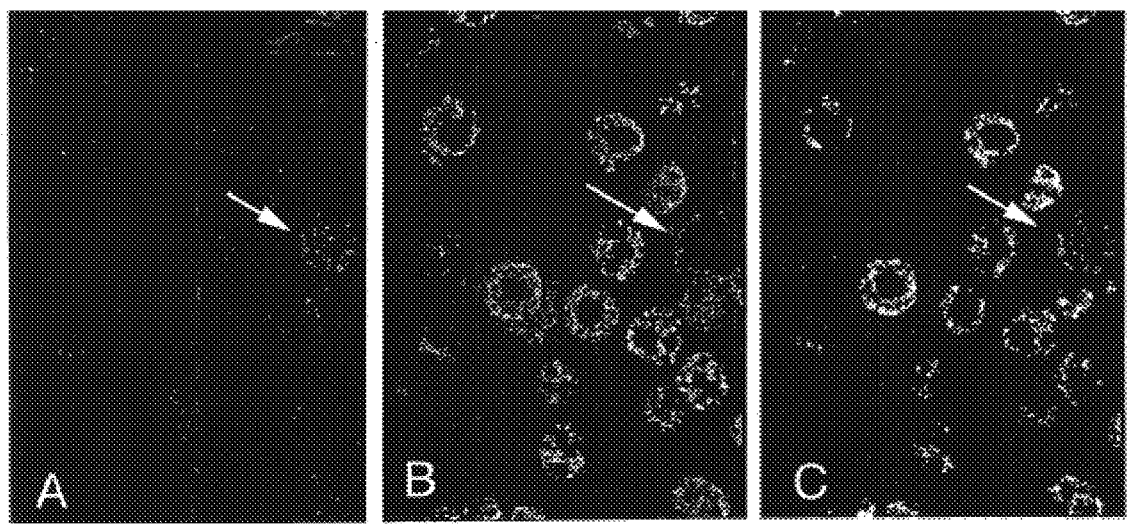

Immunostaining using CM-10A2 mouse monoclonal antibody against LANA2 on KSHV infected cell lines (BC-1, BCBL-1, BCP-1) shows a fine granular nuclear pattern in all preparations (FIG. 4). This is similar to the subnuclear distribution of LANA1 (ORF73) (11, 15, 23, 33). Double staining for LANA1 and LANA2 shows that the two proteins can co-localize to some degree but that LANA2 has a much more diffuse pattern (FIG. 5). In mitotic cells, in which LANA1 bridges viral and cellular chromosomes to allow equal viral episome segregation, LANA1 aggregates with the mitotic spindle (3). LANA2, however, is excluded from these LANA1-containing mitotic figures suggesting that LANA2 unlike LANA1, does not play an important role in episome segregation during mitosis (FIG. 5).

Figure 6:
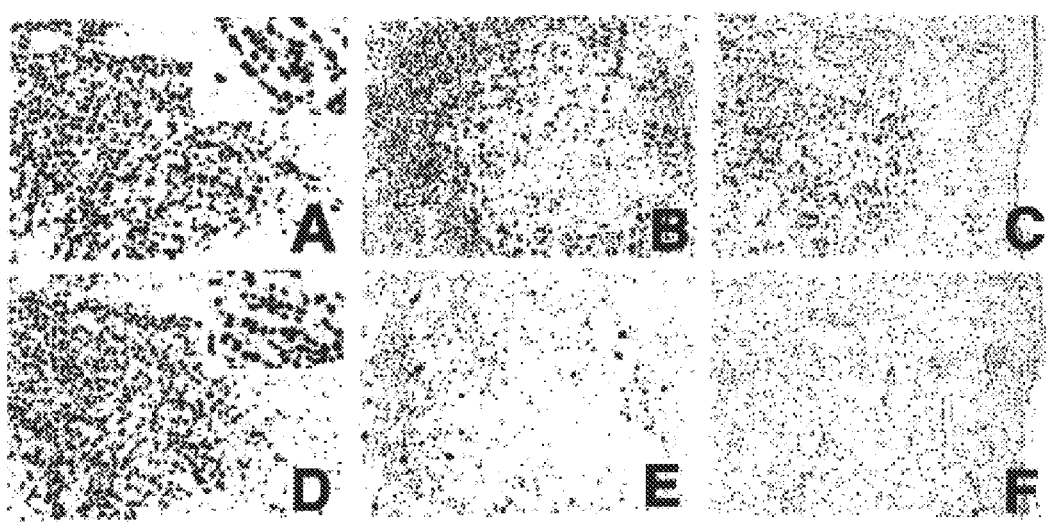

Previous studies demonstrate that some genes (e.g. ORF K9) become dysregulated in PEL tissue culture, and are expressed in established in vitro cell lines but not parental PEL tumors. Other proteins, such as vIL-6, are expressed only in situ in a minority of PEL tumor cells (32). LANA2, in contrast, is expressed in virtually all KSHV infected cells in PEL and the majority of the KSHV infected cells in Castleman's disease tumors (FIGS. 6D, E and 7B). LANA2 is not appreciably expressed in KS spindle cells taken from skin biopsies (FIG. 6F). This is most clearly seen in FIG. 7 in a lymph node containing both KS (endothelial cell origin) and CD (B cell origin) tumors. LANA2 expression in this lymph node occurs exclusively in the CD tumor cells but not KS spindle cells (FIG. 7B).

Lack of Seroreactivity to LANA2 in Serum from KSHV-Infected Patients

Unlike LANA1, LANA2 is unlikely to be a useful western blot antigen for detecting KSHV antibodies. LANA2 expressed in COS7 cells failed to react on western blotting with serum from patients with various KSHV-related disorders. None of 14 sera from individuals with AIDS-KS (n=4), classical KS (n=4), KSHV seropositive Castleman's disease (n=4) or PEL (n=2) showed serologic reactivity to LANA2 (FIG. 11). Negative control sera from four blood donors (seronegative for ORF65 and LANA1 antigens) were also non-reactive, whereas the supernatants from two mouse monoclonal LANA2 hybridoma clones (CM-10A2 and CM-8B6) were positive. We cannot exclude the possibility that other antigen formats (e.g. enzyme-linked immunoassay) might reveal a useful pattern for LANA2 seroreactivity.

LANA2 Inhibits p53 Transactivation

Since LANA1 inhibits p53-mediated transcription and apoptosis (13), we examined the effects of LANA2 on p53 function using the pG13-Luc promoter reporter (containing 13 copies of the p53 response element) transiently transfected into SAOS-2 (p53 null) osteosarcoma cells. Transient expression of 0.5 mg p53 plasmid in SAOS-2 cells resulted in an 800-fold activation of the pG13-Luc reporter which was inhibited by 87% on cotransfection of 0.5 mg pcDNA.LANA2 expression plasmid. This transcriptional repression was specific since the pGL-3 control promoter activity (FIG. 8A) as well as the activity of a Gal4 reporter plasmid (not shown) was unaffected by pcDNA.LANA2 cotransfection. This effect is not due to squelching since no transcriptional activation was seen at low levels of LANA2 expression and increasing amounts of pcDNA.LANA2 resulted in a monotonic repression of p53 activity on the pG13 reporter.

Figure 8:
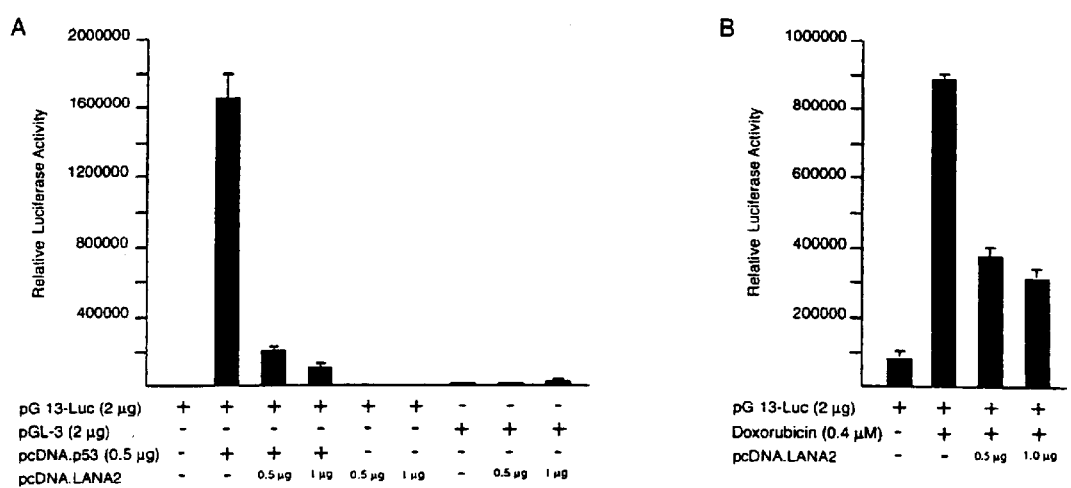

To determine if the same effect is present during endogenous p53 activation, these experiments were repeated in U2OS cells (wild-type for p53) with and without treatment with 0.4 mM doxorubicin, a chemotherapeutic agent which induces p53-mediated apoptosis. Doxorubicin treatment resulted in 13-fold activation of the pG13-Luc reporter and this effect was inhibited 57% by 0.5 mg pcDNA.LANA2 transfection (FIG. 8B).

LANA2 Protein—Protein Interactions

Figure 9:
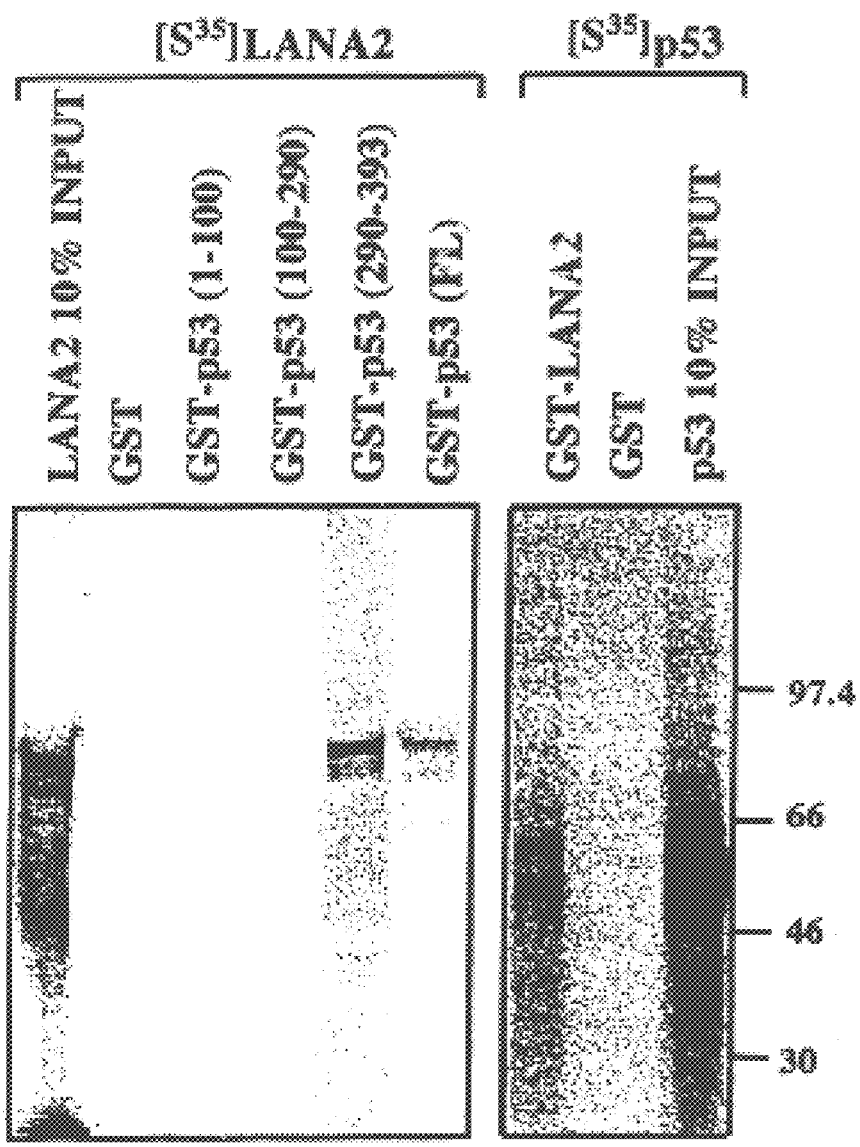
Figure 10A:
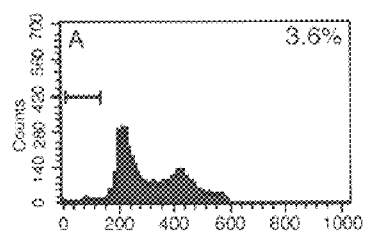
Figure 10B:
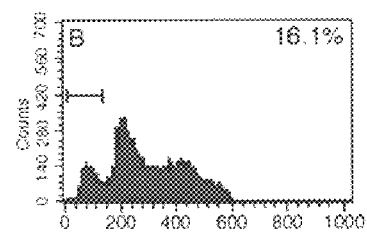
Figure 10C:
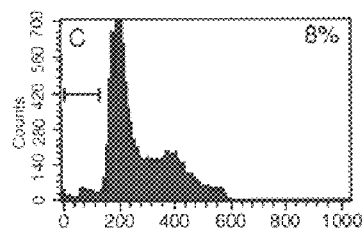
Figure 10D:
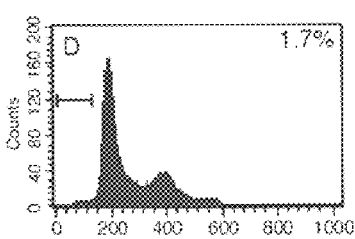
Figure 10E:
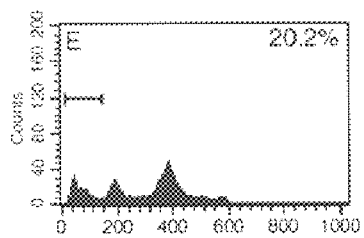
Figure 10F:
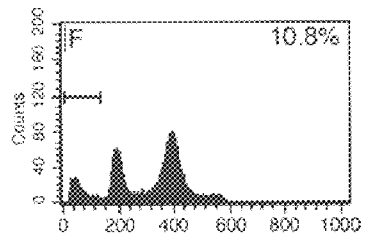

To determine if inhibition of p53 transactivation is due to direct interaction with p53 protein, we performed full length and truncated GST-p53 pulldown assays using in vitro translated [$^{35}$S]-methionine-labeled LANA2. As seen in FIG. 9, GST-p53 fusion protein precipitates LANA2 in vitro whereas no interaction is seen with GST protein alone. LANA2 interaction is localized to the region of p53 comprising aa 290–393 and no interaction occurs with the truncated p53 constructs containing aa 1–100 or aa 100–290. In the reverse pull-down experiments, GST-LANA2 but not GST alone showed specific interaction with in vitro translated full length p53.

In vivo coimmunoprecipitation experiments, however, failed to demonstrate direct interaction between LANA2 and p53 (not shown). In experiments using naturally abundant p53 from BCBL-1 cells or SAOS-2 cells in which p53 protein was overexpressed, no coimmunoprecipitation was detected for LANA2 and p53 using either LANA2 (CM-10A2 and CM-8B6) or p53 (D0-1, Pab 1801, Ab-1) monoclonal antibodies. In part these experiments were inconclusive since we noted an unusual phenomenon in that D0-1 (Santa Cruz), Pab 1801 (Santa Cruz) and Ab-1 (Oncogene) antibodies directed against p53 directly cross-react with LANA2. This was confirmed by direct western blotting with these antibodies and the bacteria-derived GST-LANA protein in the absence of p53. We thus cannot exclude artifactual p53-LANA2 interactions in the GST-pulldown assays, or that antibody binding occurs at LANA2-p53 interaction site(s) which interfers with the immunoprecipitation reaction since the binding was done under native conditions. Yeast two-hybrid assays between LANA2 and full-length p53 failed to clarify whether or not direct protein—protein interactions occur in vivo (data not shown). LANA2 cloned into the Gal4-BD cassette is toxic to the yeast and could not be evaluated. LANA2 cloned into the Gal4-AD cassette and p53 into the Gal4-BD cassette, however, shows no interaction by b-galactosidase assay.

LANA2 Inhibits p53-Mediated Apoptosis

SAOS-2 cells are null for pRB as well as p53, and overexpression of wild-type p53 in SAOS-2 cells results in apoptosis as indicated by the subdiploid fraction (20%) of cells staining with propidium iodide in a cell sorting profile (FIG. 10). In this experiment, cells were cotransfected with p53 and GFP expression plasmids, and DNA content analysis was performed only on cells gated for GFP. When LANA2 is expressed together with p53 in SAOS-2 cells (FIG. 10C), a marked diminution in subdiploid cells (from 20% to 10.8%) occurs indicating a specific inhibition of p53-mediated apoptosis and genomic fragmentation. Similar results are obtained for U20S cells, which have wild-type p53, treated with 0.4 uM doxorubicin for 30 hours, indicating that LANA2 can inhibit activation of endogenous p53 resulting from doxorubicin treatment (FIG. 10F). This was confirmed by caspase-8 activation fluorometric assays. Doxorubicin treated U20S cells transfected with pcDNA.LANA2 showed lower levels of caspase-8 activation than doxoribicin treated U20S cells transfected with pcDNA empty vector control (data not shown).

C. Discussion

LANA2 is one of the few KSHV proteins which has been found to be expressed in PEL and CD cells in vivo (11, 22, 32). However, unlike LANA1, LANA2 is not expressed in the vast majority of KS spindle cells. These findings reinforce the concept that KSHV is capable of multiple latency expression programs, and genes that are expressed in some tissues or cell lines may be silenced in others. LANA2 differs from vIL-6, another KSHV protein whose protein expression is also limited to B cells, in that vIL6 is expressed in a minority population of PEL tumor cells. Since vIL-6 is a secreted cytokine, limited expression of vIL-6 may nonetheless contribute to the pathogenesis of PEL tumors. In contrast, LANA2 expression is uniformly present in PEL tumor cells indicating that it too may have a critical role in maintaining the PEL tumor cell phenotype. These patterns of expression could be expected if the vIL-6 promoter is activated by cytokine signaling pathways that are dependent on the local cellular milieu (unpublished observation, J. Osborne, Y. Chang, P. S. Moore), whereas the LANA2 promoter is activated by B cell transcription factors.

KSHV is a gammaherpesvirus which, like EBV, has part of its natural lifecycle in CD19+ B-lymphocytes. It is apparent that a portion of the KSHV genome is devoted to maintenance of the virus in the B cell environment. B cells, for example, respond to antigen by activating immunoreceptor signaling pathways to achieve rapid clonal expansion. Under normal circumstances, induction of cell death by apoptosis occurs after B cell expansion to prevent lymphocytic hyperplasia (25). The ability of LANA2 to prevent p53-mediated B cell apoptosis would be an apparent benefit in maintaining an expanded population of infected cells, or in preventing p53 pathway activation as part of a cellular antiviral response. While our in vitro studies suggest that LANA2 inhibition of p53 activity is through direct protein—protein interaction, caution is necessary in interpreting these results since they were not confirmable through in vivo interaction assays. The p53 region binding LANA2 (aa. 290–393) in GST-pulldown assays includes the p53 tetramerization and regulatory domains, as well as residues acetylated by p300 (17), suggesting a plausible mechanism.

The reasons why KSHV possesses two latency-expressed viral proteins, LANA1 and LANA2, to target the same p53 tumor suppressor protein are unclear. LANA1 is constitutively expressed in both KS lesions as well as KSHV-infected hematopoietic tissues and therefore appears to have a broader functional spectrum than LANA2. It is important to note that our LANA2 experiments showing functional p53 inhibition were performed in osteosarcoma cell lines and so, at least under the conditions of our assays, LANA2 inhibition of p53 is not unique to B cell lines.

Regardless of the mechanism for p53-inhibition, LANA2 is a likely candidate protein involved in cell proliferation in hematopoietic tissues. Inhibition of p53-induced apoptosis may contribute to B cell hyperplasia in Castleman's disease and to cell transformation in PEL cells. Although KSHV vCYC is constitutively expressed on LT1 and LT2 in all infected cell lines, stable expression of this cyclin homolog has been difficult to achieve in vitro since it induces apoptosis (31). Direct inhibition of both pRB and p53 signaling pathways by vCYC together with LANA1 and LANA2 could theoretically contribute to proliferative/neoplastic expansion of infected B cells.

REFERENCES

1. Alexander, L., L. Denekamp, A. Knapp, M. R. Auerbach, B. Damania, and R. C. Desrosiers 2000. The primary sequence of rhesus monkey rhadinovirus isolate 26–95: sequence similarities to Kaposi's sarcoma-associated herpesvirus and rhesus monkey rhadinovirus isolate 17577. J Virol. 74:3388–98.
2. Bais, C., B. Santomasso, O. Coso, L. Arvanitakis, E. Geras Raaka, J. S. Gutkind, A. S. Asch, E. Cesarman, M. C. Gerhengorn, and E. A. Mesri 1998. G-protein-coupled receptor of Kaposi's sarcoma-associated herpesvirus is a viral oncogene and angiogenesis activator. Nature. 391:86–9.
3. Ballestas, M. E., P. A. Chatis, and K. M. Kaye 1999. Efficient persistence of extrachromosomal KSHV DNA mediated by latency-associated nuclear antigen. Science. 284:641–4.
4. Bunz, F., A. Dutriaux, C. Lengauer, T. Waldman, S. Zhou, J. P. Brown, J. M. Sedivy, K. W. Kinzler, and B. Vogelstein 1998. Requirement for p53 and p21 to sustain G2 arrest after DNA damage. Science. 282:1497–501.
5. Burysek, L., W. S. Yeow, B. Lubyova, M. Kellum, S. L. Schafer, Y. Q. Huang, and P. M. Pitha 1999. Functional analysis of human herpesvirus 8-encoded viral interferon regulatory factor 1 and its association with cellular interferon regulatory factors and p300. J Virol. 73:7334–42.
6. Burysek, L., W. S. Yeow, and P. M. Pitha 1999. Unique properties of a second human herpesvirus 8-encoded interferon regulatory factor (vIRF-2). J Hum Virol. 2:19–32.
7. Cesarman, E., Y. Chang, P. S. Moore, J. W. Said, and D. M. Knowles 1995. Kaposi's sarcoma-associated herpesvirus-like DNA sequences are present in AIDS-related body cavity based lymphomas. New Eng J Med. 332:1186–1191.
8. Chang, Y., P. S. Moore, S. J. Talbot, C. H. Boshoff, T. Zarkowska, D. Godden-Kent, H. Paterson, R. A. Weiss, and S. Mittnacht 1996. Cyclin encoded by KS herpesvirus. Nature. 382:410.
9. Davis, M. A., M. A. Sturzl, C. Blasig, A. Schreier, H. G. Guo, M. Reitz, S. R. Opalenik, and P. J. Browning 1997. Expression of human herpesvirus 8-encoded cyclin D in Kaposi's sarcoma spindle cells. J Natl Cancer Inst. 89:1868–74.
10. Dittmer, D., M. Lagunoff, R. Renne, K. Staskus, A. Haase, and D. Ganem 1998. A cluster of latently expressed genes in Kaposi's sarcoma-associated herpesvirus. J Virol. 72:8309–15.
11. Dupin, N., C. Fisher, P. Kellam, S. Ariad, M. Tulliez, N. Franck, E. van Marck, D. Salmon, I. Gorin, J. P. Escande, R. A. Weiss, K. Alitalo, and C. Boshoff 1999. Distribution of human herpesvirus 8 latently infected cells in Kaposi's sarcoma, multicentric Castleman's disease, and primary effusion lymphoma. Proc Natl Acad Sci U S A. 96:4546–51.
12. Flowers, C., S. Flowers, and G. Nabel 1998. Kaposi's sarcoma-associated herpesvirus viral interferon regulatory factor confers resistance to the antiproliferative effect of interferon-alpha. Mol Med. 4:402–12.
13. Friborg, J., Jr., W. Kong, M. O. Hottiger, and G. J. Nabel 1999. p53 inhibition by the LANA protein of KSHV protects against cell death. Nature. 402:889–94.
14. Gao, S. -J., C. Boshoff, S. Jayachandra, R. A. Weiss, Y. Chang, and P. S. Moore 1997. KSHV ORF K9 (vIRF) is an oncogene that inhibits the interferon signaling pathway. Oncogene. 15:1979–86.
15. Gao, S. J., L. Kingsley, M. Li, W. Zheng, C. Parravicini, J. Ziegler, R. Newton, C. R. Rinaldo, A. Saah, J. Phair, R. Detels, Y. Chang, and P. S. Moore 1996. KSHV antibodies among Americans, Italians and Ugandans with and without Kaposi's sarcoma. Nature Medicine. 2:925–8.
16. Godden-Kent, D., S. J. Talbot, C. Boshoff, Y. Chang, P. Moore, R. A. Weiss, and S. Mittnacht 1997. The cyclin encoded by Kaposi's sarcoma-associated herpesvirus stimulates cdk6 to phosphorylate the retinoblastoma protein and histone H1. Journal of Virology. 71:4193–8.
17. Gu, W., and R. G. Roeder 1997. Activation of p53 sequence-specific DNA binding by acetylation of the p53 C-terminal domain. Cell. 90:595–606.
18. Guan, K. L., and J. E. Dixon 1991. Eukaryotic proteins expressed in *Escherichia coli:* an improved thrombin cleavage and purification procedure of fusion proteins with glutathione S-transferase. Anal Biochem. 192:262–67.
19. Jayachandra, S., K. G. Low, A. E. Thlick, J. Yu, P. D. Ling, Y. Chang, and P. S. Moore 1999. Three unrelated viral transforming proteins (vIRF, EBNA2, and E1A) induce the MYC oncogene through the interferon-responsive PRF element by using different transcription coadaptors. Proc Natl Acad Sci U S A. 96:11566–11571.
20. Judde, J. G., V. Lacoste, J. Briere, E. Kassa-Kelembho, E. Clyti, P. Couppie, C. Buchrieser, M. Tulliez, J. Morvan, and A. Gessain 2000. Monoclonality or Oligoclonality of Human Herpesvirus 8 Terminal Repeat Sequences in Kaposi's Sarcoma and Other Diseases. J Natl Cancer Inst. 92:729–736.
21. Katano, H., Y. Sato, T. Kurata, S. Mori, and T. Sata 2000. Expression and localization of human herpesvirus 8-encoded proteins in primary effusion lymphoma, Kaposi's sarcoma, and multicentric Castleman's disease. Virology. 269:335–44.
22. Katano, H., Y. Sato, T. Kurata, S. Mori, and T. Sata 1999. High expression of HHV-8-encoded ORF73 protein in spindle-shaped cells of Kaposi's sarcoma. Am J Pathol. 155:47–52.
23. Kedes, D. H., E. Operskalski, M. Busch, R. Kohn, J. Flood, and D. Ganem 1996. The seroepidemiology of human herpesvirus 8 (Kaposi's sarcoma-associated herpesvirus): distribution of infection in KS risk groups and evidence for sexual transmission. Nature Medicine. 2:918–24.
24. Kirshner, J. R., K. Staskus, A. Haase, M. Lagunoff, and D. Ganem 1999. Expression of the open reading frame 74 (G-protein-coupled receptor) gene of Kaposi's sarcoma (KS)-associated herpesvirus: implications for KS pathogenesis. J Virol. 73:6006–14.
25. Klein, G. 1994. Epstein-Barr Virus strategy in normal and neoplastic B cells. Cell. 77:791–793.
26. Lee, H., R. Veazey, K. Williams, M. Li, J. Guo, F. Neipel, B. Fleckenstein, A. Lackner, R. C. Desrosiers, and J. U. Jung 1998. Deregulation of cell growth by the K1 gene of Kaposi's sarcoma-associated herpesvirus. Nat Med. 4:435–40.
27. Li, M., H. Lee, J. Guo, F. Neipel, B. Fleckenstein, K. Ozato, and J. U. Jung 1998. Kaposi's sarcoma-associated herpesvirus viral interferon regulatory factor. J Virol. 72:5433–40.

28. Li, M., H. Lee, D. W. Yoon, J. C. Albrecht, B. Fleckenstein, F. Neipel, and J. U. Jung 1997. Kaposi's sarcoma-associated herpesvirus encodes a functional cyclin. Journal of Virology. 71:1984–91.
29. Moore, P. S., C. Boshoff, R. A. Weiss, and Y. Chang 1996. Molecular mimicry of human cytokine and cytokine response pathway genes by KSHV. Science. 274:1739–1744.
30. Neipel, F., J. C. Albrecht, and B. Fleckenstein 1997. Cell-homologous genes in the Kaposi's sarcoma-associated rhadinovirus human herpesvirus 8: determinants of its pathogenicity?. Journal of Virology. 71:4187–92.
31. Ojala, P. M., M. Tiainen, P. Salven, T. Veikkola, E. Castanos-Velez, R. Sarid, P. Biberfeld, and T. P. Makela 1999. Kaposi's sarcoma-associated herpesvirus-encoded v-cyclin triggers apoptosis in cells with high levels of cyclin-dependent kinase 6. Cancer Res. 59:4984–9.
32. Parravicini, C., B. Chandran, M. Corbellino, E. Berti, M. Paulli, P. S. Moore, and Y. Chang 2000. Differential viral protein expression in Kaposi's sarcoma-associated herpesvirus-infected diseases: Kaposi's sarcoma, primary effusion lymphoma, and multicentric Castleman's disease. Am J Pathol. 156:743–9.
33. Rainbow, L., G. M. Platt, G. R. Simpson, R. Sarid, S. J. Gao, H. Stoiber, C. S. Herrington, P. S. Moore, and T. F. Schulz 1997. The 222- to 234-kilodalton latent nuclear protein (LNA) of Kaposi's sarcoma-associated herpesvirus (human herpesvirus 8) is encoded by orf73 and is a component of the latency-associated nuclear antigen. Journal of Virology. 71:5915–21.
34. Reed, J. A., R. G. Nador, D. Spaulding, Y. Tani, E. Cesarman, and D. M. Knowles 1998. Demonstration of Kaposi's sarcoma-associated herpes virus cyclin D homolog in cutaneous Kaposi's sarcoma by calorimetric In situ hybridization using a catalyzed signal amplification system. Blood. 91:3825–32.
35. Rodriguez, M. S., J. M. P. Desterro, S. Lain, C. A. Midgley, D. P. Lane, and R. T. Hay 1999. SUMO-1 modification activates the transcriptional response of p53. EMBO Journal. 18:6455–6461.
36. Russo, J. J., R. A. Bohenzky, M. C. Chien, J. Chen, M. Yan, D. Maddalena, J. P. Parry, D. Peruzzi, I. S. Edelman, Y. Chang, and P. S. Moore 1996. Nucleotide sequence of the Kaposi sarcoma-associated herpesvirus (HHV8) Proc Natl Acad Sci USA. 93:14862–7.
37. Sarid, R., 0. Flore, R. A. Bohenzky, Y. Chang, and P. S. Moore 1998. Transcription mapping of the Kaposi's sarcoma-associated herpesvirus (human herpesvirus 8) genome in a body cavity-based lymphoma cell line (BC-1). J Virol. 72:1005–12.
38. Sarid, R., T. Sato, R. A. Bohenzky, J. J. Russo, and Y. Chang 1997. Kaposi's sarcoma-associated herpesvirus encodes a functional bcl-2 homologue. Nature Medicine. 3:293–8.
39. Sarid, R., J. S. Wiezorek, P. S. Moore, and Y. Chang 1999. Characterization and cell cycle regulation of the major Kaposi's sarcoma-associated herpesvirus (human herpesvirus 8) latent genes and their promoter. J Virol. 73:1438–46.
40. Sun, R., S. F. Lin, K. Staskus, L. Gradoville, E. Grogan, A. Haase, and G. Miller 1999. Kinetics of Kaposi's sarcoma-associated herpesvirus gene expression. J Virol. 73:2232–42.
41. Takebe, Y., M. Seiki, J. Fujisawa, P. Hoy, K. Yokota, K. Arai, M. Yoshida, and N. Arai 1988. SRa promoter: an efficient and versatile mammalian cDNA expression system composed of the simian virus 40 early promoter and R-U5 seqment of the human T-cell leukemia virus type 1 long terminal repeat. Mol Cell Biol. 8:466–72.
42. Talbot, S. J., R. A. Weiss, P. Kellam, and C. Boshoff 1999. Transcriptional analysis of human herpesvirus-8 open reading frames 71, 72, 73, K14, and 74 in a primary effusion lymphoma cell line. Virology. 257:84–94.
43. Tanaka, N., M. Ishihara, M. Kitagawa, H. Harada, T. Kimura, T. Matsuyama, M. S. Lamphier, S. Aizawa, T. W. Mak, and T. Taniguchi 1994. Cellular commitment to oncogene-induced transformation or apoptosis is dependent on the transcription factor IRF-1. Cell. 77:829–39.
44. Zimring, J. C., S. Goodbourn, and M. K. Offermann 1998. Human herpesvirus 8 encodes an interferon regulatory factor (IRF) homolog that represses IRF-1-mediated transcription. J Virol. 72:701–7.
45. U.S. Pat. No. 4,816,567, issued Mar. 28, 1989 to Cabilly et al.
46. U.S. Pat. No. 5,225,539, issued Jul. 6, 1993 to Gregory Winter.
47. U.S. Pat. No. 5,585,089, issued Dec. 17, 1996 to Queen et al.
48. U.S. Pat. No. 5,693,761, issued Dec. 2, 1997 to Queen et al.
49. PCT International Application No. PCT/US89/05857, filed Dec. 28, 1989, published Jul. 26, 1990, WO 90/07861.

What is claimed is:

1. An isolated nucleic acid comprising the sequence of the promoter of latency-associated nuclear antigen 2 transcription as set forth in SEQ ID NO: 3.

2. A replicable vector which comprises the nucleic acid of claim 1 operably linked to a second nucleic acid which encodes a gene of interest.

3. A host vector system which comprises the vector of claim 2 and a B cell.

* * * * *